«12» United States Patent
Boussaad et al.

(10) Patent No.: US 7,638,036 B2
(45) Date of Patent: Dec. 29, 2009

(54) REDOX POTENTIAL MEDIATED CARBON NANOTUBES BIOSENSING IN HOMOGENEOUS FORMAT

(75) Inventors: Salah Boussaad, Wilmington, DE (US); Bruce A. Diner, Chadds Ford, PA (US); Janine Fan, Hockessin, DE (US); Vsevolod Rostovtsev, Swarthmore, PA (US); Ajit Krishnan, Kennett Square, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 465 days.

(21) Appl. No.: 11/240,287

(22) Filed: Sep. 30, 2005

(65) Prior Publication Data

US 2007/0227906 A1    Oct. 4, 2007

Related U.S. Application Data

(60) Provisional application No. 60/615,310, filed on Sep. 30, 2004.

(51) Int. Cl.
G01N 33/50 (2006.01)
(52) U.S. Cl. ................... 205/777.5; 204/403.01; 204/403.14; 977/920; 977/957; 435/25
(58) Field of Classification Search .......... 204/400, 204/403.01, 403.14; 205/777.5, 792; 435/4, 435/25; 977/920, 957, 958
See application file for complete search history.

(56) References Cited

U.S. PATENT DOCUMENTS 6,440,645 B1 * 8/2002 Yon-Hin et al. ............ 430/322

2007/0264634 A1 * 11/2007 Bock et al. ................. 435/6

FOREIGN PATENT DOCUMENTS

DE       101 18 200 A1    10/2002
WO      WO 02/48701 A2      6/2002
WO      WO 2004/034025 A2   4/2004

OTHER PUBLICATIONS

Berghard et al, Advanced Materials, 1998, 10(8), pp. 584-588.*
Sanjay Tyagi et al., Molecular Beacons: Probes That Fluoresce Upon Hybridization, Nature Biotechnology, vol. 14:303-308, 1996.
Philip G. Collins et al., Extreme Oxygen Sensitivity of Electronic Properties of Carbon Nanotubes, Science, vol. 287:1801-1804, 2000.
Jing Kong et al., Nanotube Molecular Wires as Chemical Sensors, Science, vol. 287:622-625, 2000.
K. Bradley et al., Charge Transfer From Adsorbed Proteins, Nano Letters, vol. 4(2):253-256, 2004.
Jong-In Hahm et al., Direct Ultrasensitive Electrical Detection of DNA and DNA Sequence Variations Using Nanowire Nanosensors, Nano Letters, vol. 4(1):51-54, 2004.
Z. Li et al., Sequence-Specific Label-Free DNA Sensors Based on Silicon Nanowires, Nano Letters, vol. 4(2):245-247, 2004.
Jun Li et al., Carbon Nanotube Nanoelectrode Array for Ultrasensitive DNA Detection, Nano Letters, vol. 3(5):597-602, 2003.
Huimin Zhang et al., Electrochemical Behavior of Multi-Wall Carbon Nanotubes and Electrocatalysis of Toluene-Filled Nanotube Film on Gold Electrode, Electrochimica Acta, vol. 49:715-719, 2004.

(Continued)

*Primary Examiner*—Kaj K Olsen

(57) ABSTRACT

Nanosensors for detecting analytes and methods of detecting analytes have been developed in which the redox potential of a redox effector in solution is altered thereby causing changes in carbon nanotube conductance. The analyte may be detected in solution, eliminating the need for immobilizing the analyte on a support.

27 Claims, 12 Drawing Sheets

OTHER PUBLICATIONS

Hongxia Luo et al., Investigation of the Electrochemical and Electrocatalytic Behavior of Single-Wall Carbon Nanotube Film on a Glassy Carbon Electrode, Anal. Chem., vol. 73:915-920, 2001.

Pichumani J. Britto et al., Improved Charge Transfer at Carbon Nanotube Electrodes, Advanced Materials, vol. 11(2):154-157, 1999.

Besteman, Koen et al., Enzyme-Coated Carbon Nanotubes as Single-Molecule Biosensors, Nano Letters, 2003, pp. 727-730, vol. 3, No. 6, American Chemical Society.

Teh, Kwok-Siong et al., A Polypyrrole-Carbon-Nanotube (PPY-MWNT) Nanocomposite Glucose Sensor, IEEE International Conference on Micro Electro Mechanical Systems, Technical Digest, Jan. 2004, pp. 395-398.

International Search Report, International Application No. PCT/US05/35544, Dated Jun. 25, 2008.

* cited by examiner

Determination of dissociation constants for inhibitors

REDOX POTENTIAL MEDIATED CARBON NANOTUBES BIOSENSING IN HOMOGENEOUS FORMAT

FIELD OF INVENTION

This invention relates to the field of nanotechnology. Specifically the invention describes a nanosensor for the detection of an analyte in which the redox potential of a redox effector in solution is altered thereby causing changes in carbon nanotube conductance. The assay takes place in solution in a homogeneous format, eliminating the need for analyte immobilization for detection.

BACKGROUND OF THE INVENTION

There is an increasing need for rapid, small scale and highly sensitive detection of biological molecules in medical, bioterrorism, food safety, and research applications. Nanostructures such as silicon nanowires and carbon nanotubes display physical and electronic properties amenable to use in miniature devices. Carbon nanotubes (CNTs) are rolled up graphene sheets having a diameter on the nanometer scale and typical lengths of up to several micrometers. CNTs can behave as semiconductors or metals depending on their chirality. Additionally, dissimilar carbon nanotubes may contact each other allowing the formation of a conductive path with interesting electrical, magnetic, nonlinear optical, thermal and mechanical properties.

It is known that single-walled carbon nanotubes are sensitive to their chemical environment, specifically that exposure to air or oxygen alters their electrical properties (Collins et al. (2000) Science 287:1801). Additionally, exposure of CNTs to gas molecules such as $NO_2$ or $NH_3$ alters their electrical conductance (Kong et al. (2000) Science 287:622). Thus chemical gas sensors can be designed on the basis of the electrical properties of carbon nanotubes such as described in DE10118200.

Sanjay and Kramer ((1996) Nature Biotech. 14:303) describe the detection of DNA in solution using molecular beacons. These are stem-loop structures that contain a fluorescence emitter and quencher, one on each strand at the base of the stem, that open in the presence of a DNA single strand or RNA, complementary to the loop region, producing an increase in the fluorescence yield of the emission. Used for real-time PCR, these structures produce a dequenching of one fluorescence emitter for every complementary nucleic acid strand hybridized.

In WO 02/48701 articles are described that use nanowires, including CNTs, to detect different types of analytes including biological analytes. The nanowire may be modified by attaching an agent that is designed to bind an analyte, the binding to the nanowire or to a coating on the nanowire then causes a detectable change in conductance. In this detection system, the interaction between the binding agent and the analyte to be detected alters the electrical conductance of the nanowire. This requirement in turn limits the functional location of the binding agent with respect to the nanowire in that they must be in close proximity, 5 nanometers or less.

Carbon nanotubes have been used in electrocatalysis. Microelectrodes constructed of multiwalled carbon nanotubes were shown to provide a catalytic surface for electrochemical reduction of dissolved oxygen, potentially useful in fuel cell applications (Britto et al. (1999) Advanced Materials 11:154). A film of single walled carbon nanotubes functionalized with carboxylic acid groups on a glassy carbon electrode showed electrocatalytic behavior with several redox-active biomolecules, involving reduction of the carboxylic acid groups (Luo et al. (2001) Anal. Chem. 73:915). Toluene-filled multiwalled carbon nanotubes as a film on a gold electrode surface were shown to respond better to electroactive biomolecules than empty carbon nanotubes (Zhang et al. (2003) Electrochimica Acta 49:715).

In WO 2004/034025 a system to measure the redox potential is described that uses a potentiometric electrochemical system based on a metal-coated silicon nanowire.

There is a need for a nanoscale detection system that has the ability to indirectly detect an analyte in a solution-based format that can provide a signal whose concentration greatly exceeds the concentration of the analyte. Applicants have solved this problem by developing a carbon nanotube based nanosensor that responds to a target analyte by altering the redox potential of a redox effector in solution, which in turn alters the redox state of the CNT and causes a change in its conductance. The concentration of redox-active effector molecules may far exceed that of the analyte. The assay is accomplished in solution and eliminates the need for immobilization of the analytes for detection.

SUMMARY OF THE INVENTION

The present invention provides a nanosensor for the detection of an analyte. The nanosensor comprises an electrically conducting path of semiconducting single-walled carbon nanotubes having a baseline conductance, in contact with an effector solution comprising a redox effector molecule. The effector solution has a given redox potential that is correlated to the redox state of the redox effector molecule. Modulations in the redox potential of the effector solution alter the conductance of the CNTs with respect to the baseline conductance, thereby producing a quantifiable signal that can be correlated to the presence of the analyte. In a first embodiment, the redox potential of the redox-active effector is changed in the presence of a redox-active analyte by a redox reporter in solution that interacts with the redox-active analyte and a co-substrate. Alternatively the redox-active analyte may itself be the redox-active effector which is acted on by the redox reporter in conjunction with a redox-active co-substrate.

In a second embodiment, a redox catalytic analyte acts on a redox-active substrate coupled to a redox-active co-substrate with one of the two substrates or an additional redox mediator acting as the effector. In a third embodiment the presence of the analyte turns on a redox-active catalyst that is modified with an activity switch, which in the absence of the analyte is turned off. Upon activation, the reporter is then able to act on a redox-active substrate coupled to a redox-active co-substrate with one of the two substrates or an additional redox mediator acting as the effector.

Accordingly the invention provides a nanosensor for detecting the presence of an redox-active analyte comprising:
a) at least two electrodes connected by an electrically conducting path comprised of one or more carbon nanotubes wherein at least one of said carbon nanotubes is semiconducting, and wherein the carbon nanotube is in contact with an effector solution having a redox potential; and
b) at least one redox reporter having a redox-active analyte as a substrate.

In an alternate embodiment the invention provides a nanosensor for detecting the presence of an redox catalytic analyte comprising:
a) at least two electrodes connected by an electrically conducting path comprised of one or more carbon nanotubes wherein at least one of said carbon nanotubes is semiconducting, and wherein the carbon nanotube is in contact with an effector solution having a redox potential; and b) a redox-active substrate that is a substrate of a redox catalytic analyte.

Alternatively the invention provides a nanosensor for detecting the presence of an analyte comprising:

a) at least two electrodes connected by an electrically conducting path comprised of one or more carbon nanotubes wherein at least one of said carbon nanotubes is semiconducting, wherein the carbon nanotube is in contact with an effector solution having a redox potential; and b) a redox reporter having an activity switch comprising an analyte receptor and a reporter inhibitor; and c) a redox-active substrate that is a substrate of the redox reporter.

In a specific embodiment the invention provides a nanosensor for detecting the presence of a redox active analyte comprising: at least two electrodes connected by an electrically conducting path comprised of one or more carbon nanotubes wherein at least one of said carbon nanotubes is semiconducting, and wherein the carbon nanotube is in contact with an effector solution having a redox potential.

Methods of using the nanosensors of the invention include:

A method for detecting a redox-active analyte comprising:

a) providing a nanosensor comprising:
  i) at least two electrodes connected by an electrically conducting path comprised of one or more carbon nanotubes wherein at least one of said carbon nanotubes is semiconducting, and wherein the carbon nanotube is in contact with an effector solution having a redox potential and wherein the carbon nanotube has a baseline conductance; and
  ii) a redox reporter having a redox-active analyte as a substrate;

b) providing a sample suspected of containing an redox-active analyte;

c) contacting the sample of (b) with the redox reporter of (a) wherein the redox potential of the effector solution is altered resulting in a change in the conductance of the carbon nanotube with respect to the baseline conductance; and d) measuring the change in conductance of the carbon nanotube with respect to the baseline conductance whereby the presence of the redox-active analyte is detected;

as well as;

16. A method for detecting a redox catalytic analyte; comprising:

a) providing a nanosensor comprising:
  i) at least two electrodes connected by an electrically conducting path comprised of one or more carbon nanotubes wherein at least one of said carbon nanotubes is semiconducting, and wherein the carbon nanotube is in contact with an effector solution having a redox potential and wherein the carbon nanotube has a baseline conductance; and
  ii) a redox-active substrate that is a substrate of a redox catalytic analyte;

b) providing a sample suspected of containing a redox catalytic analyte;

c) contacting the sample of (b) with the redox-active substrate of (a) and a co-substrate wherein the redox potential of the effector solution is altered resulting in a change in the conductance of the carbon nanotube with respect to the baseline conductance; and d) measuring the change in conductance of the carbon nanotube with respect to the baseline conductance whereby the presence of the analyte is detected;

as well as;

A method for detecting an analyte comprising:

a) providing a nanosensor comprising:
  i) at least two electrodes connected by an electrically conducting path comprised of one or more carbon nanotubes wherein at least one of said carbon nanotubes is semiconducting, and wherein the carbon nanotube is in contact with an effector solution having a redox potential wherein the carbon nanotube has a baseline conductance; and
  ii) a redox reporter having an activity switch comprising an analyte receptor and a reporter inhibitor;

b) providing a sample suspected of containing an analyte which binds to the analyte receptor of the activity switch wherein the redox reporter becomes active;

c) contacting the sample of (b) with the redox reporter of (a) wherein the redox potential of the effector is altered resulting in a change in the conductance of the carbon nanotube with respect to the baseline conductance; and d) measuring the change in conductance of the carbon nanotube with respect to the baseline conductance whereby the presence of the analyte is detected;

as well as;

A method for detecting an redox-active analyte comprising:

a) providing a nanosensor comprising at least two electrodes connected by an electrically conducting path comprised of one or more carbon nanotubes wherein at least one of said carbon nanotubes is semiconducting, and wherein the carbon nanotube is in contact with an effector solution having a redox potential and wherein the carbon nanotube has a baseline conductance;

b) providing a sample suspected of containing a redox-active analyte;

c) contacting the sample of (b) with the nanosensor of (a) wherein the redox potential of the carbon nanotube is altered resulting in a change in the conductance of the carbon nanotube with respect to the baseline conductance; and d) measuring the change in conductance of the carbon nanotube with respect to the baseline conductance whereby the presence of the analyte is detected.

In another embodiment the invention provides an activity switch for controlling the activity of an enzyme comprising an analyte receptor attached to the enzyme and an inhibitor of the enzyme linked to the analyte receptor.

Similarly the invention provides an enzyme—activity switch complex comprising an enzyme comprising:

i) an analyte receptor; and ii) an enzyme inhibitor;

wherein the analyte receptor is linked to the enzyme and the enzyme inhibitor is fixed to the portion of the analyte receptor distal to its attachment to the enzyme, and wherein the inhibitor is bound to the active site of the enzyme.

A method of using the activity switch is provided comprising:

a) providing an enzyme—activity switch complex comprising an enzyme comprising:
  i) an analyte receptor; and
  ii) an enzyme inhibitor;

wherein the analyte receptor is linked to the enzyme and the enzyme inhibitor is fixed to the portion of the analyte receptor distal to its attachment to the enzyme, and
wherein the inhibitor is bound to the active site of the enzyme;

b) contacting the enzyme—activity switch complex of step (a) with an analyte that has affinity for the analyte receptor, whereby the analyte binds the analyte receptor, removing the inhibitor from active site of the enzyme; and c) detecting the activity of the uninhibited enzyme of step (b)

BRIEF DESCRIPTION OF THE FIGURES AND SEQUENCES

The invention can be more fully understood from the following detailed description and the accompanying sequence descriptions, which form a part of this application.

The sequence descriptions and content of the sequence listing attached hereto (additionally provided in a computer readable form) are incorporated by reference as a part of this application. The sequences and Sequence Listing comply with the rules governing nucleotide and/or amino acid sequence disclosures in patent applications as set forth in 37 C.F.R. §1.821-1.825 ("Requirements for Patent Applications Containing Nucleotide Sequences and/or Amino Acid Sequence Disclosures—The Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The Sequence Descriptions contain the one letter code for nucleotide sequence characters and the three letter codes for amino acids as defined in conformity with the IUPAC-IYUB standards described in *Nucleic Acids Research* 13:3021-3030 (1985) and in the *Biochemical Journal* 219 (No. 2):345-373 (1984) which are herein incorporated by reference. The symbols and format used for nucleotide and amino acid sequence data comply with the rules set forth in 37 C.F.R. §1.822.

SEQ ID NO:1 is oligo 27 and oligo 28 with sequence derived from the LDLR gene.

SEQ ID NO:2 is oligo 32.

SEQ ID NO:3 is oligo 50.

SEQ ID NO:4 is oligo 61.

Figure 10:
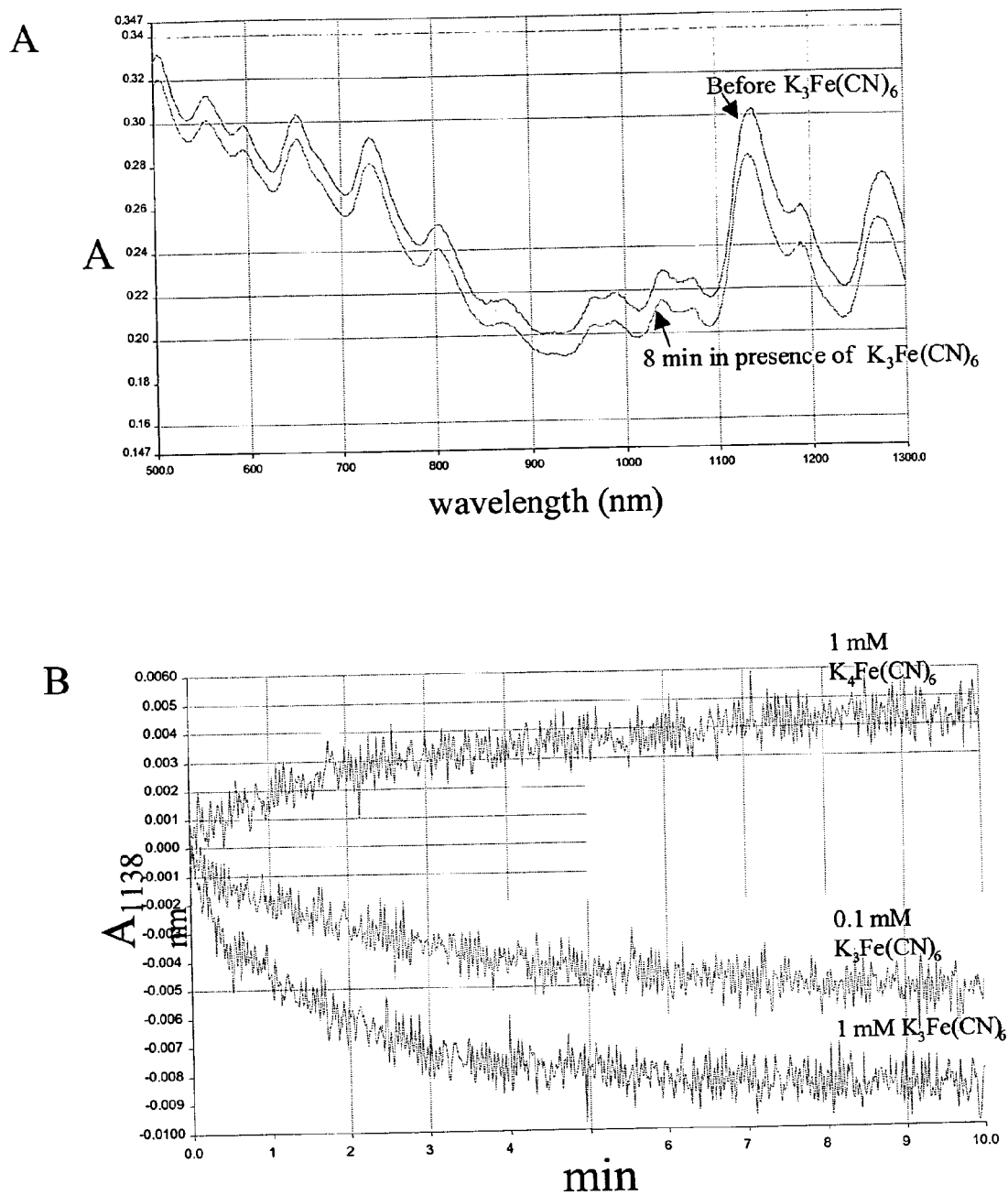

FIG. 10 shows (A) a spectrum of HiPco carbon nanotubes before and 8 min after the addition of 1 mM $K_3Fe(CN)_6$; (B) a time course of the evolution of the absorption at 1138 nm of surfactant dispersed HiPco carbon nanotubes following the addition of 0.1 and 1.0 mM $K_3Fe(CN)_6$ and 1 mM $K_4Fe(CN)_6$.

Figure 11:
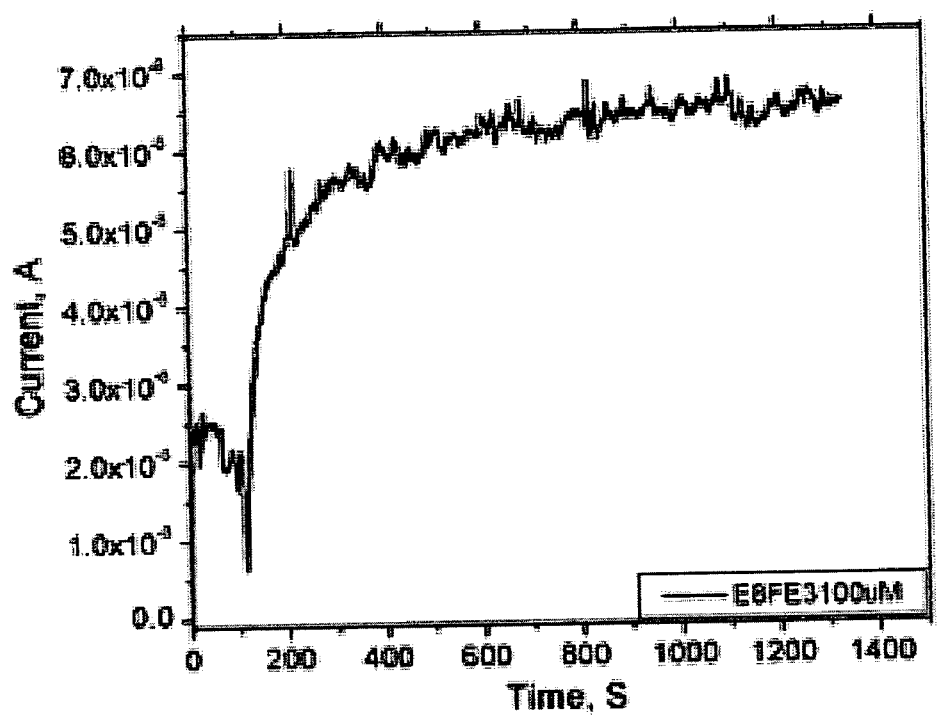

FIG. 11 shows a time course of the evolution of the conductance of CVD grown carbon nanotubes following the addition of 0.1 mM $K_3Fe(CN)_6$. Vsd=50 mV, Vg=−0.2 V.

Figure 12:
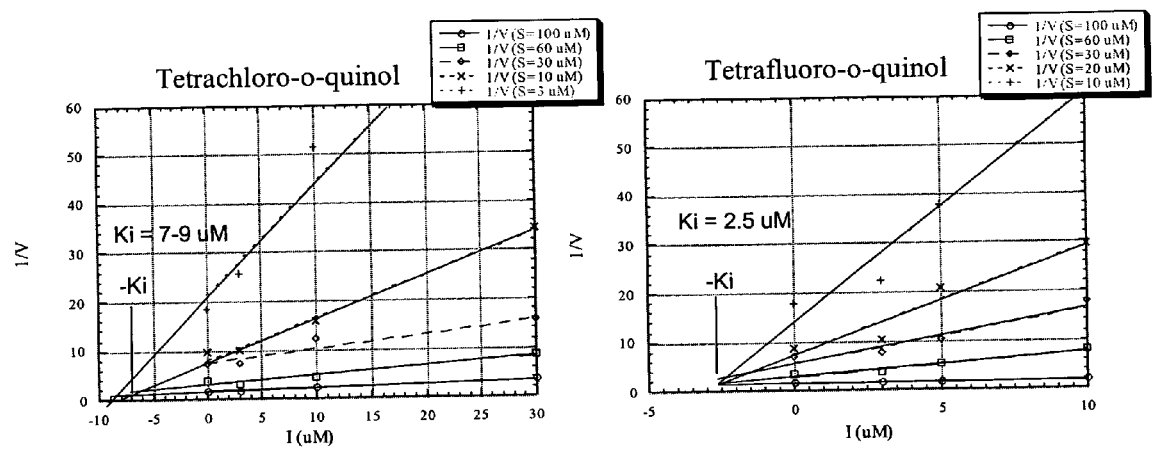

FIG. 12 plots the rate of $ABTS^{-2}$ oxidation with varying inhibitor concentration for (A) tetrachloro-o-quinol and (B) tetrafluoro-o-quinol.

DETAILED DESCRIPTION

The present invention provides nanosensors for the detection of analytes. Typically analytes of the invention are biomolecules. In the present invention, CNTs are used to detect the presence of an analyte by responding to a change in the redox potential of an effector molecule in solution. CNTs of the nanosensor are provided with a baseline conductance which will evolve with changes in the redox potential of the effector molecule. The main elements of the nanosensor of the invention are:

An electrically conducting path between at least two electrodes comprised of at least one semiconducting CNT where the CNT has a baseline conductance;

An effector solution in contact with the CNT where the effector solution establishes a redox potential around the CNT; and Optionally, a redox reporter, typically a catalyst, that oxidizes or reduces a redox substrate at the expense of a co-substrate. An analyte may itself be the redox reporter.

In contrast to previous methods, the detection does not involve direct binding of the target biomolecule on or in close proximity to the CNTs. The redox potential of the effector is changed by a redox reporter interacting with an analyte that is a redox-active substrate, or a redox-active substrate which interacts with a redox catalytic analyte. Alternatively, an analyte activates an inhibited redox reporter in the presence of a redox-active substrate. A redox-active co-substrate is present in all cases. The interaction, which alters the redox potential of the effector, changes the conductance of at least one semiconducting CNT in contact with a solution containing the effector molecules. The redox-active analyte substrate, a redox-active co-substrate, or a redox mediator acts as the redox effector. Advantages of this detection system are that 1) the target analyte alone or in a complex with a reporter molecule does not need to be attached to or be in close proximity to the CNT and 2) the effect caused by the presence of the analyte is magnified relative to the concentration of the analyte.

The present invention provides methods for detecting an analyte indirectly by introducing a redox reporter and redox-active co-substrate, a redox-active substrate and co-substrate, or an inhibited redox reporter, redox-active substrate and co-substrate that interact with a target analyte causing a change in redox potential of an effector, and then measuring the change in conductance of at least one CNT in a conductive path that is in contact with a solution containing the effector. In addition, the analyte itself may be redox active and directly cause a change in conductance.

Highly sensitive nanoscale detection of biomolecules has utility in bioterrorism, biomedical, environmental, food safety, research, and other applications. Use of the present system wherein detection by the CNTs is of a change in redox potential in solution increases the diversity of biomolecules that may be assayed and the sensitivity of detection. Samples may be screened to detect a target biomolecule that would provide information regarding a bioterrorism agent, a disease agent, a genetic disorder, an environmental contaminant, a food pathogen, a desired product, and other such components.

The following definitions and abbreviations are to be used for the interpretation of the claims and the specification.

"CNT" means carbon nanotube.

"$ABTS^{-2}$" refers to 2,2'Azino-di-(3-ethylbenzthiazoline-sulfonate)

The term "nanotube" refers to a single-walled hollow cylinder having a diameter on the nanometer scale and a length of several micrometers, where the ratio of the length to the diameter, i.e., the aspect ratio, is at least 5. In general, the aspect ratio is between 100 and 100,000.

By "carbon-based nanotube" or "carbon nanotube" herein is meant a single-walled hollow cylinder composed primarily of carbon atoms.

The term "baseline conductance" refers to the conductance of a carbon nanotube comprised within a nanosensor of the invention, measured prior to the addition of the sample or at the earliest time following the addition of a solution potentially containing the analyte for detection. The baseline conductance provides a measurement that can be compared to the conductance measurement made when the analyte is being detected.

The term "analyte" or "target analyte" means the substance that is the object of detection by the nanosensor. Analytes may be a variety of materials and substances but are typically biomolecules and the production of biological reactions and events. A "redox catalytic analyte" for example is an analyte that has a catalytic function that has the potential of altering the redox potential of a solution. Redox catalytic analytes are often enzymes. Alternatively a "redox active analyte" is an analyte that may directly affect the redox potential of a solution.

The term "reporter" or "redox reporter" will mean a catalytic substance capable of reacting with a substrate and co-substrate to alter the redox potential of the effector solution. The redox reporter may be chemically or catalytically based. Typical redox reporters of the invention are enzymes such as glucose oxidase that interact with a substrate (glucose) and a co-substrate (oxygen).

The term "redox-active substrate" and "redox-active co-substrate" or "co-substrate" refer to substrates of the redox reporter. The reaction of the redox-active substrate with a redox-active co-substrate is catalyzed by a redox reporter. In this case, one of the two substrates is oxidized and the other reduced.

The term "activity switch" refers to an aspect of a reporter molecule that allows permits the presence of an analyte to activate the reporter. Typically the activity switch comprises two elements, an "analyte receptor" and an "inhibitor". The analyte receptor generally will incorporate the inhibitor. In the absence of analyte the activity switch function to inhibit the reporter in that the inhibitor blocks the active site of the reporter. In the presence of an analyte the activity switch is modified such that the inhibitor is removed from the active site and the reporter is activated. "Analyte receptors" are any element that can be fixed to the reporter and that will bind the analyte. Additionally the analyte receptor must be able to comprise the inhibitor. Typical analyte receptors are biomolecules such as oligonucleotides, peptides, proteins, and peptide nucleic acids. Where the reporter is an enzyme, inhibitors will be enzyme inhibitors.

The term "homogeneous" as used in conjunction with the nanosenor and methods of the invention refers to a sensor or method that makes use of reagents in solution. The term "homogeneous catalysis" refers to catalysis by a free catalytic moiety in a solution.

The term "target biomolecule" refers to a substance to be detected in a biological sample, or a sample potentially containing biological material. The target biomolecule is an analyte that is part of a sample.

The term "effector" or "redox effector" refers to a molecule in the effector solution that is in redox equilibrium with the carbon nanotubes. The redox effector may be directly the redox-active substrate or co-substrate, or an additional molecule, the redox mediator, in equilibrium with one of these that can interact most rapidly and reversibly with the CNTs, poising their redox potential and causing a change in their conductance.

The term "effector solution" means the solution comprising the effector molecule that is in contact with the CNT comprised within the nanosensor of the invention. The effector molecule may be either one or both of the redox active substrate or the co-substrate in either the oxidized or reduced form.

The term "redox mediator" refers to a redox molecule whose redox potential is in equilibrium with the redox state of a redox-active substrate and which, as an effector, causes a change in the CNT conductance.

The term "redox potential" refers to an electrochemical potential characterized by the log of the ratio of the concentrations of the oxidized to the reduced forms of a redox molecule, according to the Nernst equation.

The term "charge carrier" refers to any molecule or other discrete entity that has the ability to receive or donate electrons and carry a charge.

The term "source electrode" will mean one of the three terminals of a field effect transistor from which the majority carrier flows into the transistor.

The term "drain electrode" will mean one of the three terminals of a field effect transistor through which the majority carrier exits the transistor.

The term "gate electrode" will mean one of the three terminals of a field effect transistor which, by means of an electric field, controls the flow of charge carriers in the transistor, thereby controlling the output current.

The term "surface" refers to any material located at the solid-liquid interface.

The term "support" refers to any material comprised within the nanosensor that will serve as a support for the various elements of the sensor, such as the CNTs. Supports may take a variety of shapes and are composed of a variety of type of materials including polymers, matrices and gels.

The term "polypeptide" refers to a chain of amino acids which may be an entire protein or may be a portion thereof. Polypeptides may be natural or synthetic, and may include one or more artificial chemical analogues of a naturally occurring amino acid. For the purposes of this description, a peptide is considered to be a type of polypeptide and a polypeptide is a type of protein.

The term "laccase" refers to a multi-copper oxidoreductase enzyme (EC 1.10.3.2) that catalyzes the four-electron reduction of $O_2$ to $H_2O$ with the concomitant one-electron oxidation of a substrate. Laccase is particularly suitable for use in the enzyme switch composition of the present invention.

An "oligonucleotide" or "oligo" is a polymer of RNA, DNA, or peptide nucleic acid (PNA). It optionally contains synthetic, non-natural or altered nucleotide bases. The base sequence of an oligonucleotide probe is complementary to the sequence of the portion of the target nucleic acid molecule to which hybridization is desired. An oligonucleotide probe may also be used to bind to a nucleic acid binding protein. In this case, it may be double-stranded if interaction with the binding protein requires a double-strand structure. An oligonucleotide may also be covalently linked to a protein.

The term "peptide nucleic acid" refers to a material having nucleotides coupled together by peptide linkers.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein. The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above, except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater is the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8).

Nanosensors

The nanosensors of the invention involve a homogeneous reporting system for the detection of an analyte. Typically the nanosensor comprises the following elements:

An electrical conducting path between at least two electrodes comprised of at least one semiconducting CNT where the CNT maintains a baseline conductance;

An effector solution in contact with the CNT where the effector solution establishes a redox potential around the CNT; and Optionally, a redox reporter, typically a catalyst, that oxidizes or reduces a redox substrate at the expense of a co-substrate.

Figure 1:
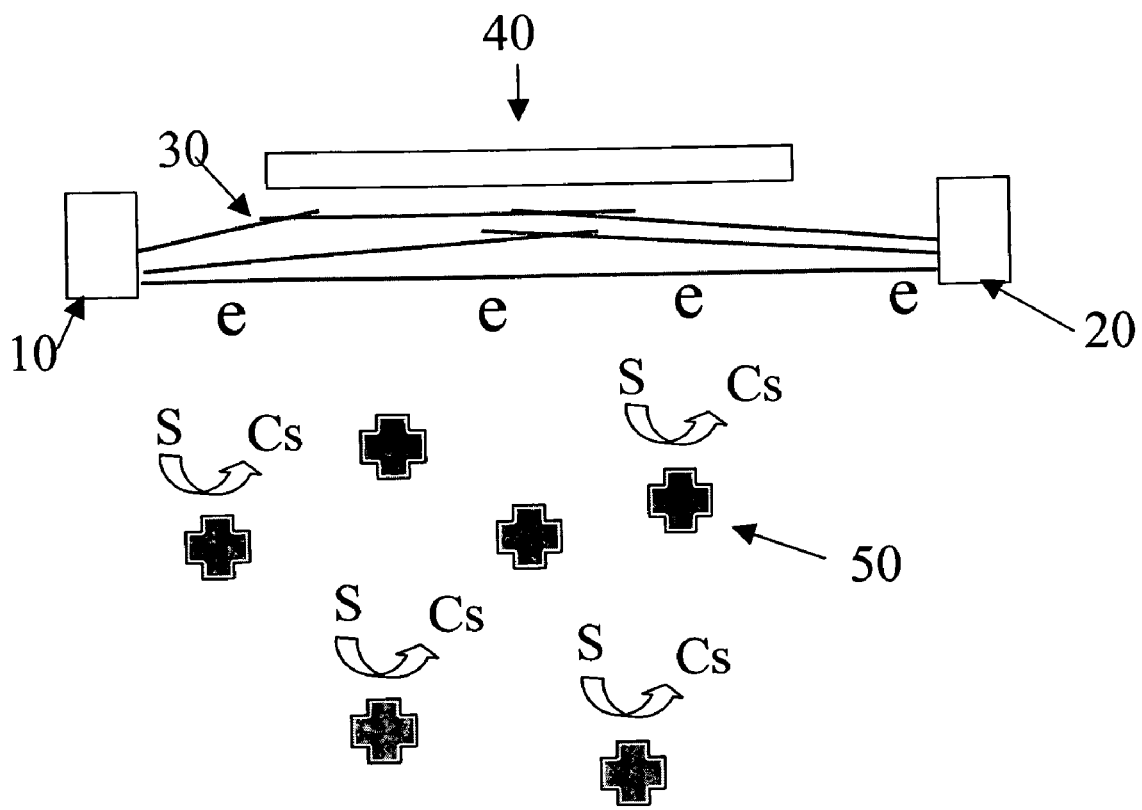
FIG. 1 is a diagram of a nanosensor embodiment that includes a redox reporter in solution.

The invention may best be understood by making reference to the diagrams. For example, one embodiment is shown in FIG. 1. The nanosensor comprises two electrodes (10,20) connected by an electrically conducting path comprising at least one semiconducting CNT (30). The CNT (30) inherently possesses a baseline conductance. The electrodes (10, 20) may be independently either source or drain. The CNT (30) is in association with an effector solution (e) which has a redox potential. The nanosensor additionally may comprise a gate electrode (40) which generates an electric field to gate the conductance of the CNTs. An analyte is introduced to the nanosensor which is a redox-active analyte. The analyte is itself a redox active substrate (S) and is acted upon by a redox reporter (50), in conjunction with an added redox active co-substrate (Cs). The redox active substrate (S), which is also the analyte, and co-substrate (Cs) are each either oxidized or reduced producing an alteration of the redox potential of the effector solution. Changes in the redox potential of the effector solution produce a corresponding change in the conductance of the CNT which can be measured to determine the presence of the analyte.

Figure 2:
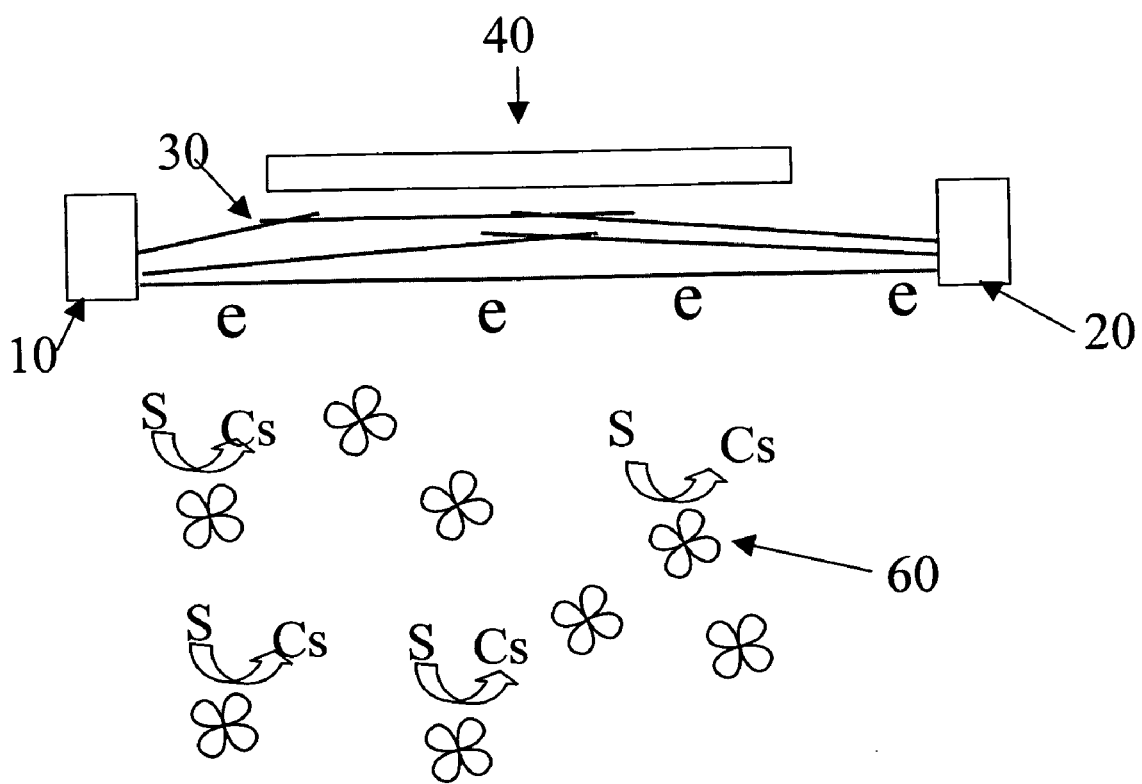
FIG. 2 is a diagram of a nanosensor embodiment where the analyte is itself a redox reporter able to react with a redox-active substrate and redox-active co-substrate, the redox potential of one of which is preferentially sensed by the nanotubes.

Another embodiment applicable to the detection of a redox catalytic analyte is shown in FIG. 2. The basic elements of the nanosensor are as illustrated in FIG. 1. A redox catalytic analyte (60) functions as a reporter and acts on an added redox-active substrate (S) and co-substrate (Cs) that are designed to interact with the redox catalytic analyte. As in the format described in FIG. 1, introduction of the redox active substrate (S) and a co-substrate (Cs) results in the oxidation of the substrate (S) and the reduction of the co-substrate (Cs) (or vice versa) producing an alteration of the redox potential of the effector solution which is detected as a change in conductance in the CNT.

Figure 3:
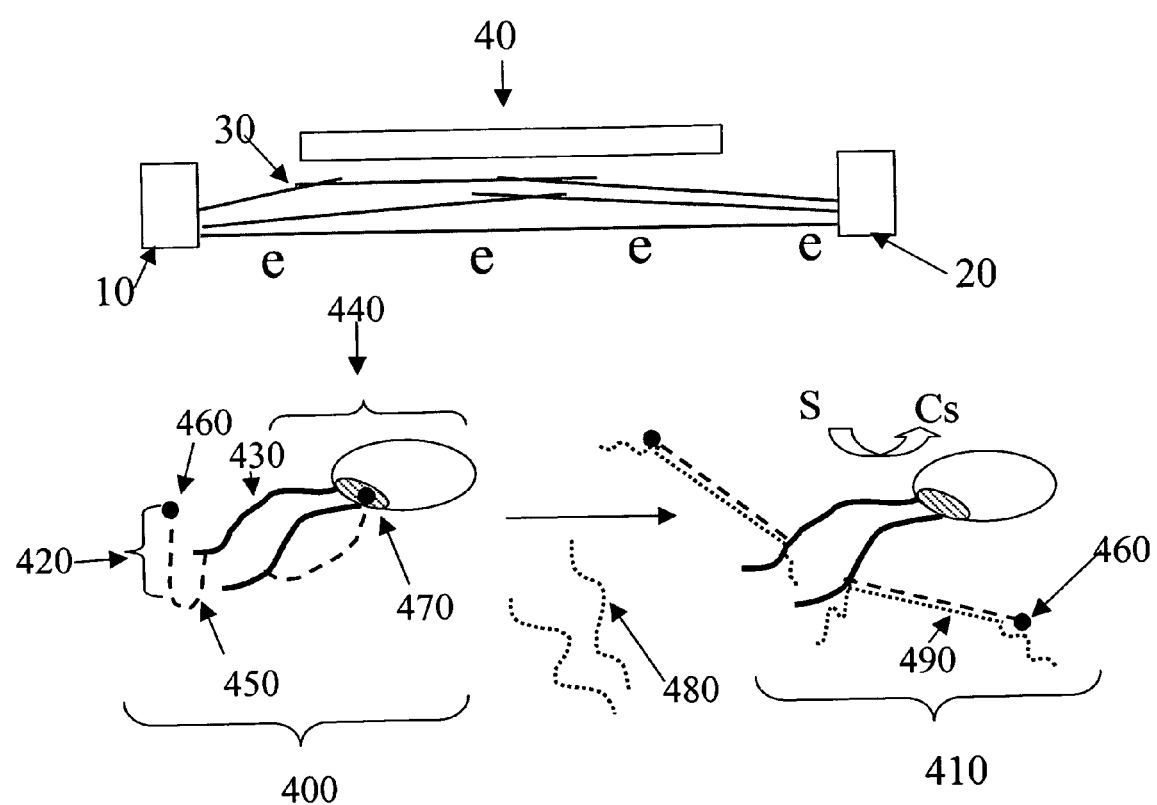
FIG. 3 is a diagram of a nanosensor embodiment with a modified redox reporter that is turned on by the binding of a nucleic acid analyte.

In those instances where the reporter is catalytic, the invention provides a format for the nanosensor where the reporter may be activated and "switched on" by the presence of an analyte. Analytes suitable for detection via an activity switch reporter will be those that have the ability to interact with the reporter and "switch on" the reporter. This format employs what is referred to herein as an "activity switch" and allows greater flexibility in the design of the sensor. A specific embodiment of the activity switch is illustrated in FIG. 3. The basic elements of the nanosensor are as illustrated in FIG. 1. In this embodiment the redox reporter is an enzymatic glycoprotein (440), and may exist in either an active (410) or inactive (400) form. One aspect of the glycoprotein (440), is the presence of a point of attachment for an activity switch (420), such as an oligosaccharide chain (430). The activity switch comprises an oligonucleotide (450) which is an analyte receptor anchored via its 5' end to the glycoprotein (440), and an inhibitor (460) attached to the oligo at the 3' end. The oligonucleotide is highly flexible and in its single stranded form is able to bend such that the inhibitor binds to the active site of the protein (470) resulting in the inactive form (400)

the enzymatic glycoprotein (440). When the inhibited reporter comes in contact with a nucleic acid analyte (480) that is complementary to a portion of the anchored oligo analyte receptor (450) the resulting hybridization (490) pulls the inhibitor (460) away from the active site of the glycoprotein (440), thus switching on the enzyme, and allowing the oxidation/reduction of the substrate (S) and/or Co-substrate (Cs).

In an additional embodiment the analyte is redox-active and changes the redox potential of the effector solution in contact with the CNT with no need for a redox reporter. Optionally a redox mediator may be added in this embodiment to enhance the change in redox potential of the effector solution.

In each of these embodiments no immobilization of the analyte is necessary for detection, greatly enhancing the utility of the assay over those methods performed in heterogeneous format for some applications.

Carbon Nanotubes of the Nanosensor

The nanosensor of the invention comprises at least one semiconducting CNT comprised within an electrically conducting path. CNTs have diameters on the nanometer scale and a ratio of the length to the diameter, i.e., the aspect ratio, of at least 5. In general, the aspect ratio is between 100 and 100,000. Carbon nanotubes are single-walled hollow cylinders composed primarily of carbon atoms. CNTs of the nanosensors of the invention may be doped with agents such as metals and may have coatings. Preferred CNTs are free or substantially free of metals. By "substantially free" it is meant that metals are only detectable in trace amounts where such amounts are so low as to have no effect on the electrical conductance of the CNT.

CNTs may be produced by a variety of methods known to those skilled in the art, and are additionally commercially available. Methods of CNT synthesis include laser vaporization of graphite (A. Thess et al. (1996) *Science* 273:483), arc discharge (C. Journet et al. (1997) *Nature* 388:756) and HiPCo (high-pressure carbon monoxide) process (P. Nikolaev et al. (1999) *Chem. Phys. Lett.* 313:91). Chemical vapor deposition (CVD) can also be used for producing carbon nanotubes (J. Kong et al. (1998) *Chem. Phys. Lett.* 292: 567; J. Kong et al. (1998) *Nature* 395:878; A. Cassell et al. (1999) *J. Phys. Chem.* 103, 6484-6492; H. Dai et al. (1999) *J. Phys. Chem.* 103:11246).

Additionally CNTs may be grown via catalytic processes both in solution and on solid substrates (Yan Li, et al. (2001) *Chem. Mater.* 13(3):1008; N. Franklin and H. Dai (2000) *Adv. Mater.* 12:890; A. Cassell et al. (1999) *J. Am. Chem. Soc.* 121:7975).

Preferred in the invention are single-walled CNTs. The CNTs are placed in a conducting path between two electrodes, generally the source and drain. A variety of types of CNTs may be used where at least one of the CNTs between source and drain electrodes is semiconducting to provide an electrically conducting path that can be controlled by a gating electrode. Multiple CNTs of varying chirality may be joined to provide the electrically conducting path.

The CNTs may be suspended between the source and drain electrodes of the nanosensor, or supported on a support surface. The surface may be comprised of any non-conductive material. Examples include, but are not limited to, silicon, polysilicon, silicon dioxide, silicon nitride, polymeric materials, glass, agarose, nitrocellulose, nylon, and insulating materials. Particularly useful are silica chips. Typically silica chips have a thin layer of natural oxide, which has very low electrical conductivity and is an insulator. For better insulation of the surface from the underlying silica, a thicker oxide layer that is typically about 500-600 nm may be added, by a method such as with a thermal treatment in air. This provides additional insulation from the underlying silica.

A gating electrode in the nanosensor generates an electric field to change the CNT conductance such that the sensitivity of the CNTs to the presence of the effector can be optimized. The gate is an electrode separated from the CNT by a dielectric material and polarized relative to the drain electrode. The gate may be for example a back gate, top gate or split gate for operation in air. An electrode that contacts a solution in the CNT chamber may be used for operation as a liquid gate.

Since the redox potential of an effector in solution provides the signal for detection by the CNT, there is no requirement for close proximity between the CNT and the analyte. This feature allows the CNT to be in any location accessible either by diffusion or flow, including such as by pumping and injecting, of the effector in solution. For example, the CNT may be in the same chamber where the effector concentration is changed, or in a separate chamber. The surface of the CNT may be functionalized or coated to enhance or increase the specificity of the detection of the redox potential of the solution. Coatings such as PEG, PEI, PFE, polylysine, polyglutamic acid, and polystyrene sulfonic acid may be added to control non-specific binding or the binding of charged species.

The exact structure of the nanosensor is not specified by the nanosensor of the invention. Any sensor structure may be employed with the components of the invention wherein the CNT comes in contact with the solution in which a redox potential is changed.

Analytes

Analytes that are targets may be, for example, chemicals and biomolecules. Biomolecules are particularly suitable analyte targets of the invention. Any biomolecule that is redox-active, can act as a redox-active substrate or is redox catalytic can be an analyte for the purposes of the invention. Additionally, any analyte, that can interact with the analyte receptor in an activity switch such that the redox reporter modified with the activity switch is activated, is an analyte for the purposes of the invention. A target biomolecule may for example be an enzyme that catalyzes a redox reaction, a metabolite that acts as a redox-active substrate and an analyte that is redox-active such as ascorbate and permanganate. In addition, a target biomolecule may be a nucleic acid that can bind the analyte receptor in an activity switch such that the redox reporter modified with the activity switch is activated. The nucleic acid may be DNA, PNA (peptide nucleic acid) or any type of RNA, for example ribosomal RNA, messenger RNA, and antisense RNA. If the analyte is a double stranded nucleic acid, prior to detection, the double stranded DNA is melted into two free single strands. Binding of a nucleic acid single strand and the steps that follow are carried out below the melting temperature.

Redox Reporter

The redox reporter may be any molecule that promotes electron transfer between the redox active substrate and co-substrate, thereby modifying the redox potential of the redox effector. Redox reporters are often catalysts. Enzymes may be used as redox reporters and redox active molecules may be their substrates. The enzymatic redox reporter catalyzes a reaction involving the redox active substrate and co-substrate such that there is a change in the redox potential of the effector solution.

Enzymes that may be used as redox reporters, and molecules that are their substrates and co-substrates are, for example, laccase and phenols/$O_2$, $ABTS^{2-}/O_2$, glucose oxidase and glucose/$O_2$; cholesterol oxidase and cholesterol/$O_2$; bilirubin oxidase and bilirubin/$O_2$; alcohol dehydrogenase and alcohols/$NAD^+$; lactate dehydrogenase and lactate/DCPIP (dichlorophenol indophenol); D-amino acid oxidase and D-alanine/$O_2$.

If the analyte is itself an enzyme that catalyzes a reaction involving a redox-active substrate and co-substrate, then no additional redox reporter is required in the nanosensor (as in FIG. 2). However, if neither the redox-active substrate nor the co-substrate transfer electrons readily with the CNTs, then an additional redox mediator may be used to provide such coupling.

Activity Switch

The redox reporter may be modified to include an activity switch that can regulate the enzymatic activity of the redox reporter. The activity switch of the present invention has two components: an inhibitor that binds to the active site or to an allosteric site of an enzyme thereby blocking its activity, and an analyte receptor that binds to the target analyte. An enzyme having an activity switch is an activity switch derivatized enzyme.

The analyte receptor of the activity switch may be attached to the enzyme directly to the protein. Direct attachment may be, for example, through a lysine using an amine group, through a cysteine using a thiol group, through as aspartic acid or a glutamic acid using a carboxyl group by methods known to one skilled in the art. If the enzyme has oligosaccharide chains (a glycoprotein), the activity switch may be attached to these chains. For example, the enzymatic glycoproteins glucose oxidase and laccase, have oligosaccharide chains which are locations for activity switch attachment.

In the present invention, the analyte receptor may be any molecule which can bind to the target analyte and which allows the inhibitor to access the active site or allosteric site in the free state but does not allow access upon binding to the target analyte. The analyte receptor may be, for example, a protein, a polypeptide, an oligopeptide, a peptide nucleic acid, an oligonucleotide, a polynucleotide or any type of nucleic acid. Preferred is a single stranded oligonucleotide probe, attached via the 5' end to the reporter molecule and linked at the 3' end to an inhibitor of the enzyme activity. It is understood that the attachments at the 5' and 3' ends can be switched without impact on the function. Any methods for attaching compounds to DNA, and DNA to proteins may be used to prepare an enzyme switch. The oligonucleotide, which is highly flexible in its single stranded form, is able to bend such that the inhibitor binds to the active site or to the allosteric site, blocking the action of the enzyme on its reporter substrate. Upon hybridization of the complementary strand of the analyte DNA (or RNA) to the enzyme-bound oligonucleotide probe, the double stranded DNA (or DNA/RNA hybrid) is now much more rigid than the single strand, with a persistence length some 60-fold greater than that of the single stranded probe oligonucleotide. The inhibitor can then no longer bind to the active site or to the allosteric site of the enzyme, which is consequently turned on (an example is shown in the diagram in FIG. 3). One skilled in the art will know the length of analyte receptor required to have stable hybridization and the conditions of the assay required to maintain the double strand during detection. It is particularly useful for hybridization of the oligonucleotide analyte receptor to the analyte nucleic acid to drive the dissociation of the inhibitor from its binding site. This occurs when the decrease in free energy associated with hybridization of the analyte receptor to the analyte exceeds that associated with the binding of the inhibitor to the enzyme.

The enzyme inhibitor of the activity switch must be linked to the analyte receptor. Linkage may be of the inhibitor compound directly, or may involve derivatization of the inhibitor to provide a functional group for linkage. For example, the laccase inhibitors tetrachloro-o-quinol and tetrafluoro-o-quinol, described below, may be derivatized with a functional group, such as an aldehyde group, to allow linking to the analyte receptor. Thus inhibitors include an inhibitory compound that must have a functional group added so that it can be linked to the analyte receptor, as well as compounds that have a functional group through which linkage can occur. Where a functional group is added to allow linkage, the functional group must be added so as not to block the portion of the compound that is active in inhibition. For example, the quinol in the tetrafluoro-o-quinol laccase inhibitor may not be functionalized since this group interacts with copper at the active site of laccase. An inhibitor is particularly useful when the dissociation constant of the inhibitor for its binding site on the enzyme is substantially lower than that of the substrate for its binding site, which may or may not be at the same site. This difference in dissociation constant provides that the inhibitor is able to prevent the substrate from binding. The inhibitor may be a competitive inhibitor, or a non-competitive inhibitor.

The enzyme controlled by the activity switch is one to which an analyte receptor with a linked inhibitor may be attached. Some examples are laccase, bilirubin oxidase, and glucose oxidase. A preferred embodiment of the activity switch is an oligonucleotide analyte receptor attached at one end to laccase and at the other end to a laccase inhibitor. Laccases (E.C. 1.10.3.2) are a group of multi-copper oxidoreductases (Systematic Name: Benzenediol:oxygen oxidoreductase). These enzymes are capable of removing electrons from a wide range of substrates. In all reactions, however, the enzyme performs a four-electron reduction of molecular $O_2$ to form $H_2O$. For a general review of laccases, see for example: Dawson, C. R. and Tarpley, W. B. The copper oxidases. In: Sumner, J. B. and Myrback, K. (Eds.), The Enzymes, $1^{st}$ ed., vol. 2, Academic: New York, 1951, p 454-498; Malmstrom, B. G. et al., Copper-containing oxidases and superoxide dismutase. In: Boyer, P. D. (Ed.), The Enzymes, $3^{rd}$ ed., vol. 12, Academic: New York, 1975, p 507-579; Mayer, A. M. and Harel, E. *Phytochem.* 18:193-215 ((1979); Nakamura, T. *Biochim. Biophys. Acta* 30:44-52 and 538-542 (1958); Reinhammar, B. and Malmstrom, B. G. "Blue" copper-containing oxidases. In: Spiro, T. G. (Ed.), Copper Proteins, Wiley: New York, p 109-149 (1981). For insight into the crystal structure of a laccase, see, for example, Bertrand, T. et al. (*Biochemistry.* 41(23):7325-7333 (2002)).

Laccases are widely distributed throughout nature, occurring in plants, fungi, yeasts and bacteria; however, the best known laccase producers are of fungal origin, since these enzymes are particularly well-studied due to their natural role in both the polymerization and depolymerization of lignin. As such, some fungal laccases suitable for the purposes of the present invention herein include (but are not limited to) those isolated from *Ascomycetes* and *Basidiomycetes*. More specifically, illustrative sources of fungal laccases include those from: *Aspergillus, Neurospora, Podospora, Botrytis, Collybia, Fomes, Lentinus, Pleurotus, Trametes, Rhizoctonia, Coprinus, Psaturella, Myceliophthora, Schytalidium, Polyporus, Phlebia, Coriolus, Hydrophoropsis, Agaricus, Cascellum, Crucibulum, Myrothecium, Stachybotrys and Sporormiella*. Most preferred are *Trametes versicolor, T. villosa, Myceliophthora thermophilia, Stachybotrys chartarum,*

*Coriolus hirsutus* and *C. versicolor*. Most preferred are commercially available laccases available from sources such as Wacker Chemie (München, Germany; *T. versicolor*), Novozymes (Franklinton, N.C.; *M. thermophilia*), Genencor (Palo Alto, Calif.; *S. chartarum*), Sigma-Aldrich (St. Louis, Mo.; *C. versicolor*) and SynectiQ (Dover, N.J.; *C. hirsutus*).

The source of laccase is not limiting to the invention herein. Thus, although fungal laccases are preferred, laccases can also be obtained from transgenic yeasts (e.g., *Pichia, Saccharomyces* and *Kluyveromyces*), transgenic fungi (e.g., *Aspergillus, Trichoderma* or *Chrysosporium*) and transgenic plants that serve as production hosts to express laccase genes cloned from other organisms (e.g., of fungal origin). Additionally, laccase may be produced from a variety of bacteria (e.g., *Escherichia, Bacillus* and *Streptomyces*).

Additionally non-native laccases may also be used in the invention herein. These modified laccases can be obtained by traditional mutagenesis (e.g., chemical, UV) or directed evolution methods (e.g., in vitro mutagenesis and selection, site-directed mutagenesis, error prone PCR, "gene shuffling"), wherein the techniques are designed to alter the amino acid sequence of the protein with the objective of improving the characteristics of the laccase. Examples of improvements would include altering substrate specificity or increasing the stability of the native enzyme.

Laccase inhibitors are any chemical compounds that can bind to laccase and inhibit the enzymatic activity. Effective inhibitors have a high reduction potential such that they are not easily oxidized. Specifically, an effective laccase inhibitor has a reduction potential that is more positive than the reduction potential of the copper centers of the laccase enzyme. The reduction potential of different laccases, from different sources as described above, may have different reduction potentials which are readily known or measured by one skilled in the art. For example, the reduction potential of the *Trametes versicolor* laccase is known to be 0.78-0.79 V vs. NHE. Thus, for example, ortho-hydroxy-quinols with reduction potentials of at least about 0.79 were found to be effective inhibitors of *Trametes versicolor* laccase. Preferred laccase inhibitors are tetrachloro-o-quinol, tetrafluoro-o-quinol, 3,4-dihydroxy-2,6-dichloro-benzaldehyde, and a substituted hydrazone of 3,4-dihydroxy-2,6-dichloro-benzaldehyde. Preferred attachment of the inhibitor to DNA is through a maleimide group on maleimide-dPEG$_4$-NHS ester converted to a hydrazide by reaction with hydrazine and coupled to 3,4-dihydroxy-2,6-dichloro-benzaldehyde to form the hydrazone. Preferred attachment of DNA to laccase is by aldehyde-hydrazide attachment chemistry.

Redox Effector and Redox Mediator

As has been discussed above, the redox reporter of the invention reacts with a redox-active substrate and co-substrate to change the redox potential of an effector solution comprising an effector molecule. In one embodiment the effector molecule may be either the substrate or co-substrate. Optionally the effector molecule may be another molecule. Redox species that can interact rapidly and reversibly with CNTs to alter their conductance may be a redox effector (also called effector herein). The redox effector is a molecule whose redox potential is changed under the influence of the redox reporter. The redox effector may be either one of the two redox reporter substrates (redox-active substrate and co-substrate), or may be another molecule. Generally, one of the substrates acts as an electron donor or acceptor and the co-substrate undergoes reduction or oxidation, respectively. The redox potential of one of the substrates may then be sensed by the CNTs because it is able to donate or accept electrons rapidly and reversibly to or from the nanotubes. This species is the redox effector. The other substrate may react slowly or not at all with the CNTs. This species is less visible to the CNTS. The log of the ratio of the concentration of the oxidized to the concentration of the reduced form of the redox effector determines its solution redox potential.

Both substrates must be present for analyte detection. One may already be present and not require separate addition such as when oxygen acts as one of the substrates.

A redox mediator that is not itself a substrate may be added as an effector. For example, if neither substrate from the redox reporter reaction is effective in substantially changing the CNT conductance, a redox mediator may be desirable. An example of a redox mediator is DCPIP (dichlorophenol indophenol) which may be reduced by the bound flavin of lactate dehydrogenase (redox reporter) in which lactate (substrate) is oxidized and the bound flavin (co-substrate) is reduced. DCPIP(ox)/DCPIP(red) can then act rapidly and reversibly with the CNTs to change their redox potential. Molecules that may function as mediators include, but are not limited to, o-quinones, p-quinones, dichlorophenol indophenol (DCPIP), 2,2'-azino-bis(3-ethylbenz-thiazoline-6-sulfonate ($ABTS^{-2}$), nicotinamide adenine dinucleotide ($NAD^+$/NADH), phenazine, phenoxazine and phenothiazine derivatives, and Os-complexes.

Redox Potential

Any redox species in solution that can interact rapidly and reversibly with CNTs to alter their conductance is applicable to this invention. Applicants have found that single-walled semiconducting carbon nanotubes show redox behavior as a general property, such that the concentration of charge carriers of the CNT is reversibly sensitive to redox molecules capable of oxidizing and/or reducing the CNT. Depending on the redox potential (proportional to the log of the ratio of the oxidized to the reduced state), an electron transfer reaction can take place between the redox molecules and the carbon nanotube, hence changing the density of charge carriers of the nanotube, which in turn causes a shift in the source-drain current vs. gate voltage plot. For example, the oxidation of the nanotube by a suitable oxidant results in an increase in the hole concentration in the valence band, which shifts the Isd vs gate voltage toward positive gate voltages. Likewise, the reduction of the nanotube by a suitable reductant decreases the concentration of holes in the valence band and therefore shifts the plot toward negative gate voltages. This phenomenon is applicable to the monitoring of any redox process, preferably to sense the presence of biomolecules using the nanosensors and methods of the present invention.

Samples

Samples that may be assayed for the presence of an analyte using nanosensors and methods of the present invention include biological samples as well as non-biological samples. For example, a sample may be from a cell, tissue or fluid from a biological source including a human, an animal, a plant, fungus, bacteria, virus, etc. The source of a sample is not limited and may be from an environmental source, from food or feed, produced in a laboratory, or other source.

Method for Analyte Detection

In the method for analyte detection, a sample having a redox active analyte is placed in contact with a redox reporter, or a sample having a redox catalytic analyte is placed in contact with a redox-active substrate, and the redox potential of an effector solution is changed as a result. A redox active co-substrate and/or a redox mediator may also be added. In addition, a redox active analyte may be detected without the need for a redox reporter, optionally in the presence of a redox mediator. Alternatively, the analyte is placed in contact with a redox-active substrate, a co-substrate, and a redox reporter that is modified with an activity switch such that it is initially inactive, and it is activated in the presence of the analyte, whereby the redox potential of an effector solution is changed. The solution with the altered effector redox potential may already be in contact with the CNT or the solution with the altered effector redox potential is brought in contact with the CNT. The solution containing the effector may flow through a channel, tubing, or other conduit to come in contact with the CNT.

The conductance of the CNT is measured and compared to a measure of the CNT conductance that was taken prior to adding the sample or at the earliest time following the addition of the sample. Measurement of the CNT conductance is generally made by applying a dc (direct current) bias voltage between the source and drain electrodes while varying the gate voltage. In addition, the signal to noise ratio may be improved by ac (alternating current) modulation of the bias voltage. Alternatively, the CNT conductance is measured by holding the gate voltage constant and recording the current as a function of time. A gate electrode is preferred but not required.

EXAMPLES

The present invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "µL" means icroliter(s), "mL" means milliliter(s), "nm" means nanometer(s), "mm" means millimeter(s), "cm" means centimeter(s), "µm" means micrometer(s), "mM" means millimolar, "M" means molar, "V" means volts, "mV" means millivolts, "Vg" means gate voltage, "Vsd" means source-drain voltage, "Isd" means source-drain current, "p-type" means charge carrier type (e.g. hole), "CVD" means chemical vapor deposition.

Example 1

Oxidation and Reduction of a Single-Walled Carbon Nanotube Device

Nanotube devices, prepared as follows, were purchased from Molecular Nanosystems (Palo Alto, Calif.). Single-walled carbon nanotubes were grown from catalyst pads in a CVD furnace at 900° C. The catalyst pads were patterned on a thermally oxidized surface (500 nm thick) of a (100) silicon wafer. After the growth, less than or equal to 5 nm of Ti, 50 nm of Pd and less than 50 nm of Au layers were deposited sequentially onto the $SiO_2$/Si surface to form electrical contacts with the nanotubes.

The metallic nanotubes present in the gap (2 micron) were destroyed, by ramping the bias voltage from 0 to 10V while holding the back gate voltage at 0V. This procedure, performed in air, enhanced the ON-Off ratio of the devices to ~3-4 orders of magnitude. The electronic properties of the remaining semiconducting nanotubes were monitored by applying a fixed bias voltage between the source and drain electrodes while changing the back gate voltage.

Figure 4:
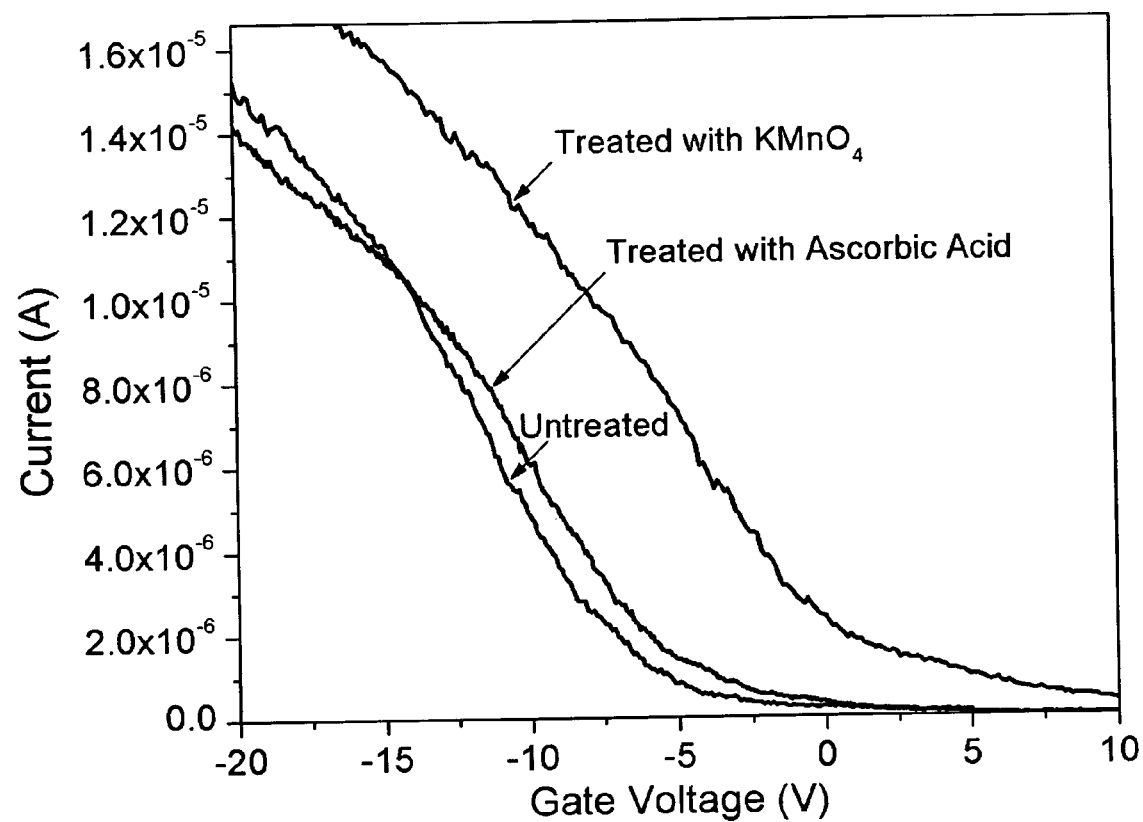
FIG. 4 shows the current vs gate voltage characteristics of single-walled carbon nanotubes treated with $KMnO_4$ and ascorbic acid. The measurements were performed in air using a back gate.

The source-drain current vs gate voltage characteristics of a semiconducting single-walled carbon nanotube device recorded using a back gate in air were determined for untreated and redox molecule treated devices (FIG. 4). The curve labeled "Untreated" shows the Isd vs. Vg characteristics of the device with no further treatment. A drop (~20 µL) of 100 µM of $KMnO_4$ was placed on top of the carbon nanotube device for ~15 min and then rinsed with ultrapure deionized water (EASYpure II, Barnstead Inc. Dubuque, Iowa). After drying with a gentle stream of $N_2$, the Isd vs. Vg curve was again recorded. As shown by the curve labeled "Treated with $KMnO_4$", this treatment produced a significant shift of the current vs gate voltage characteristics to positive gate voltages. This shift is due to the oxidation of the carbon nanotube by permanganate ions, which increases the concentration of free p-type carriers. The carbon nanotubes of the device were re-reduced by treatment with a similar sized drop of 100 mM of ascorbic acid placed on top of the device and similarly incubated, rinsed and dried. As shown by the curve labeled "Treated with Ascorbic acid", this treatment produced a shift of the Isd vs. Vg characteristics back to the original position. This shift is due to the decrease in the concentration of the p-type charge carriers through reduction by ascorbic acid. This example illustrates that redox molecules were able to modulate the electronic properties of single-walled carbon nanotube devices.

Example 2

Sensitivity of the Conductance of a Single-Walled Carbon Nanotube Device to Solution Redox Potential A flow cell of 4.4 µl volume was mounted and sealed around a carbon nanotube device using an O-ring. The flow cell allowed the device to come in contact with different solutions.

Figure 5:
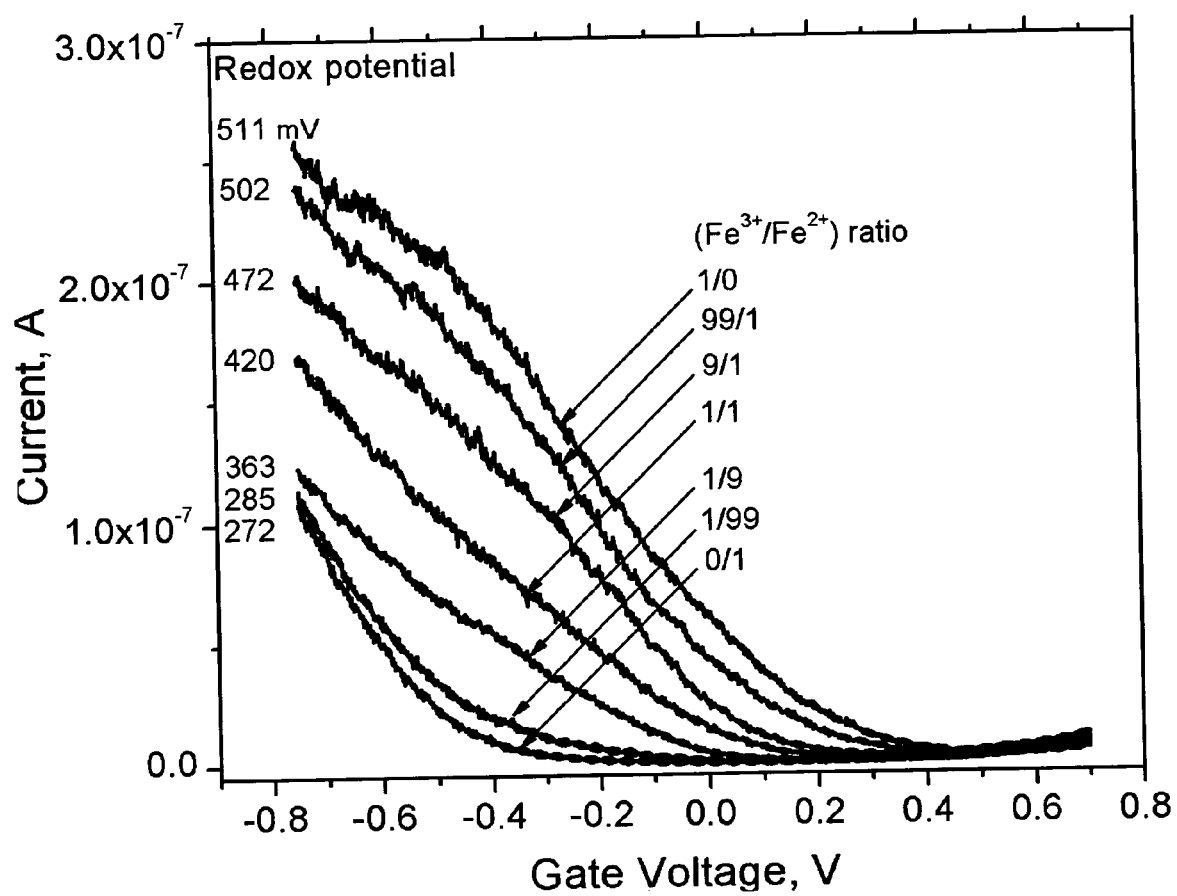
FIG. 5 shows the current vs gate voltage characteristics of a single-walled carbon nanotube device recorded at various redox potentials.

The source-drain current vs gate voltage characteristics were recorded on a single-walled semiconducting carbon nanotube device covered in 50 mM glycine buffer, pH 9.0. An electrode adjacent to the device and in contact with the same solution was used as a liquid gate and scanned from +0.7 to −0.75 V. The source-drain voltage was fixed at 50 mV. A family of buffer solutions was prepared containing various ratios of $K_3Fe(CN)_6$ to $K_4Fe(CN)_6$, the concentrations of which totaled 1 mM. The redox potential of each solution was measured using a Pt and Ag/AgCl combination redox electrode (Orion model 967800). Listed in FIG. 2 are the redox potentials of each solution expressed versus the standard hydrogen electrode (SHE). Each solution was separately placed in the flow cell in contact with the carbon nanotube device and the current vs gate voltage characteristics were recorded in each case using liquid gate scanning. The Isd vs. Vg curves were increasingly turned on at higher gate potentials as the solution redox potential was increased (FIG. 5). This behavior reflects the oxidation and reduction of the carbon nanotubes of the device, with ferri- ($K_3Fe(CN)_6$) and ferrocyanide ($K_4Fe(CN)_6$), respectively, such that as the redox potential increases the concentration of free p-type carriers increases. This behavior was fully reversible, which indicated the ability of the carbon nanotubes to interact with both redox species. Thus this device can be used as a reversible redox sensor of the solution redox potential. This behavior in aqueous solution is in contrast to the data shown in FIG. 4 where the carbon nanotube device was probed in air.

Example 3

Streptavidin and Biotinylated Laccase Coatings on a Chip Containing Single-Walled Carbon Nanotube Devices Silicon chips were prepared for patterned CVD growth of single-walled carbon nanotubes and metal electrode deposition (Molecular Nanosystems, Palo Alto, Calif.). A thermal oxide layer of 500 nm thickness covers the heavily doped silicon, which acts a backgate. A nanotube device was incubated overnight at room temperature and then for 24 h at 4° C. in a solution of 1 mg/ml of streptavidin (Molecular Probes) in PBS in a sealed and humidified Petri dish. The chip washed with water and then incubated for 40 min with biotinylated laccase. The latter was prepared by treatment of 0.48 mg/ml *Trametes versicolor* laccase (Wacker Chemie, Munich, Germany) with 120 mM $NaIO_4$ in 50 mM $NaHCO_3$, pH 7.4 for 60 min at room temperature. The laccase was then washed using a Centricon 30 (Millipore) with 50 mM $Na_2CO_3$, pH 9 to remove the remaining $NaIO_4$ and reacted with 250 µM biotin-cadaverine and 5 mM $NaBH_3CN$ for 2 h at room temperature. The laccase was then washed with 50 mM MES pH 5.5 to remove the unreacted small molecules.

Figure 6:
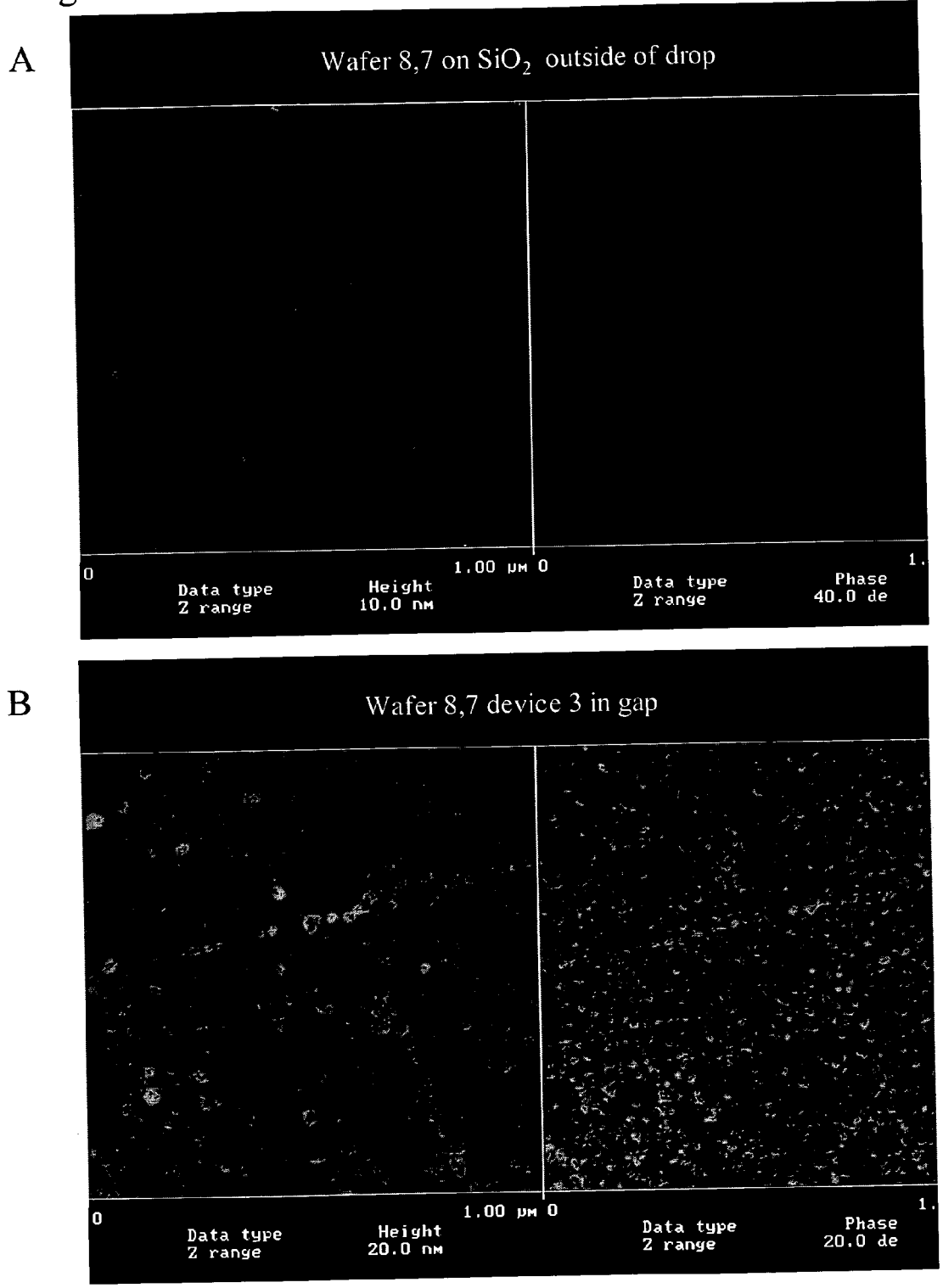
FIG. 6A shows an AFM image of $Si/SiO_2$ chip (A) outside of region containing streptavidin coated with biotinylated laccase and 6(B) inside region containing streptavidin coated with biotinylated laccase.

The biotinylated laccase was then bound to the streptavidin layer by incubation for 40 minutes at a concentration of 2.1 mg/mL in 50 mM MES pH 5.5. The unbound laccase was then removed by rinsing with ultrapure deonized water. This treatment produces a monolayer coating of laccase tightly bound to the chip due to the biotin-streptavidin interaction ($Kd=10^{-15}$ M). After the 40 min incubation with laccase, the chip was rinsed with ultrapure deionized water and placed into the flow cell for the electrical characterization described in Example 4. After completing the electrical characterization, the chip was stored in a humidified Petri dish and then examined by atomic force microscopy. Images of the laccase monolayer bound to streptavidin are shown in FIG. 6. FIG. 6A shows the region outside the drop where the strepatavidin was deposited onto the chip. The silica surface is quite smooth and free of debris. FIG. 6B shows the region where the streptavidin and biotinylated laccase were placed. The surface is coated with a regular carpet of protein, which, from its thickness, is likely to be a monolayer of streptavidin and laccase.

Example 4

Figure 7:
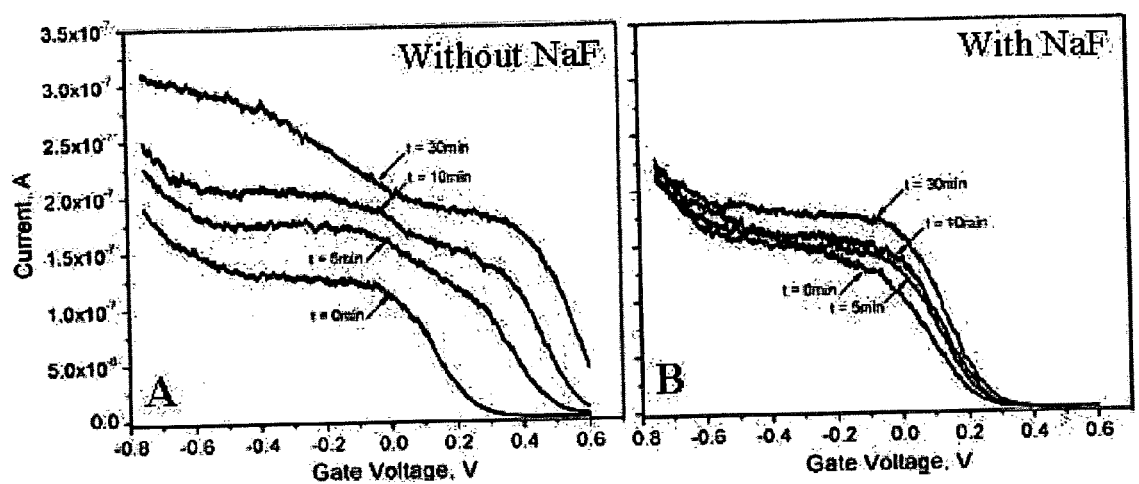
FIG. 7 shows the current vs gate voltage characteristics of a single-walled carbon nanotube device coated with streptavidin and bound to biotinylated laccase: (A) exposed to a 30 µM $ABTS^{-2}$ solution in 50 mM Glycine pH 3.0; (B) exposed to a 30 µM $ABTS^{-2}$ solution in 50 mM Glycine pH 3.0 with 1 mM NaF.

Redox Enzyme-Mediated Oxidation of a Redox Mediator Sensed Via the Conductance of a Single-Walled Carbon Nanotube Device The flow cell was mounted on the single-walled carbon nanotube device that was coated with streptavidin and bound with biotinylated laccase, prepared in Example 3, and the source-drain current vs gate voltage characteristics of the laccase coated device were measured by liquid gating using an electrode adjacent to the single-walled carbon nanotube device. The device in 50 mM Glycine pH 3.0 exhibited an Isd vs. Vg curve similar to that in the same buffer in the absence of laccase. Upon injection of a 30 µM solution of the redox mediator and laccase substrate $ABTS^{-2}$ (2,2'-azino-bis(3-ethylbenz-thiazoline-6-sulfonate) diammonium salt, Em=650-680 mV) in 50 mM Glycine pH 3.0, the Isd vs. Vg curve first shifted toward negative gate voltages (FIG. 7A, curve t=0 min). This behavior is due to the reduction of the carbon nanotubes by $ABTS^{2-}$. Upon incubation, there is a continuous shift of the Isd vs. Vg curves to positive gate voltages, in the direction opposite to that of the first shift. This positive shift is a consequence of the redox activity of the laccase which oxidizes $ABTS^{2-}$ to $ABTS^{-1}$, at the same time reducing $O_2$ to $2H_2O$. The activity of the redox enzyme results in an increase of the concentration of $ABTS^{-1}$ in the solution, thereby increasing the solution redox potential. The increasing redox potential, in turn, oxidizes the carbon nanotubes, increasing the concentration of p-type charge carriers and causing the Isd vs. Vg curve to shift to positive gate voltages. To prove that these changes are indeed a consequence of laccase activity, 1 mM NaF was added to inhibit the redox activity of the laccase enzyme. As described in Example 5 and shown in FIG. 8, this concentration of NaF inhibits the laccase activity by 95%. FIG. 7B shows the evolution of the Isd vs. Vg curve for the same carbon nanotube device, monitored as a function of time under the same conditions as for FIG. 7A except for the presence of 1 mM NaF. The plots presented in FIG. 7B show a much reduced shift with time of the Isd vs. Vg curve to positive gate voltages. This experiment clearly demonstrates that single-walled carbon nanotube devices can be used for redox-coupled sensing of biomolecules. The presence of an analyte can cause a redox enzyme to be bound to the device after which the presence of the enzyme can be detected by its redox activity on a suitable redox-active substrate. Alternatively, the redox enzyme can be prebound to the surface of the device such that it can detect the presence of a redox-active analyte by oxidation or reduction of the analyte. In both cases the enzyme activity produces a change in the solution redox potential, detected by the device

Example 5

Inhibition of Laccase Activity by NaF

Figure 8:
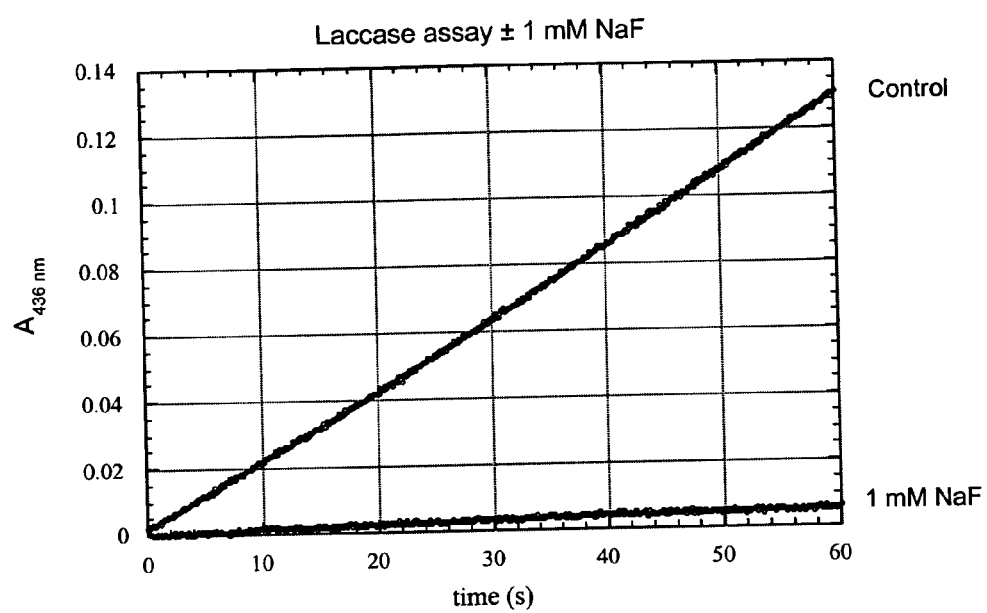
FIG. 8 shows the oxidation of $ABTS^{-2}$ by laccase in 50 mM Glycine pH 3. The measure of absorbance at 436 nm tracks the formation of $ABTS^{-1}$ in the presence and absence of 1 mM NaF.

A stock solution of *Trametes versicolor* laccase (4.8 mg/ml) was diluted 200,000-fold into 50 mM Glycine, pH 3.0. At time zero, $ABTS^{-2}$ (2,2'-azino-bis(3-ethylbenzthiazoline-6-sulfonate) diammonium salt was added at a concentration of 5 mM and the oxidation of $ABTS^{-2}$ was followed by monitoring the absorbance change at 436 nm. Shown in FIG. 8 is the result of the laccase assay in the presence and absence of 1 mM NaF. The latter inhibits the laccase activity by 95%.

Example 6

Redox Sensing at a Distance from the Carbon Nanotube Device

Figure 9:
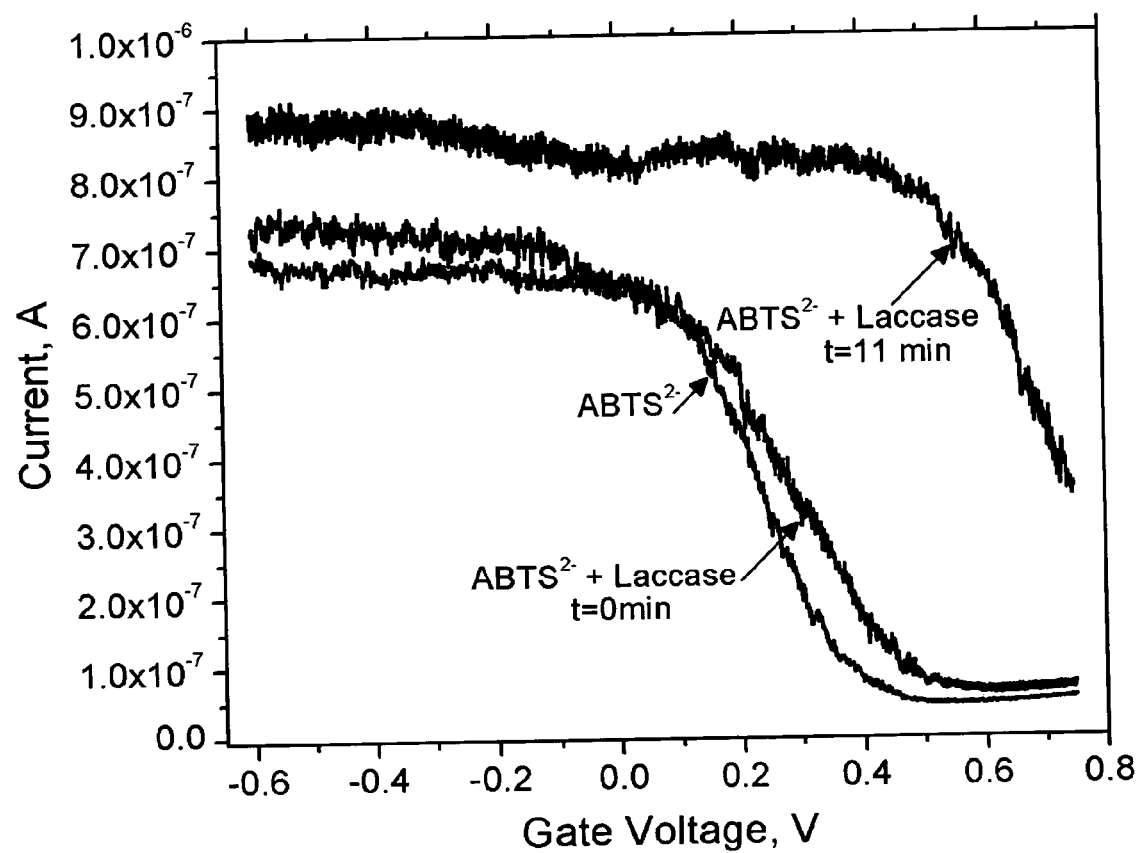
FIG. 9 shows source-drain current vs gate voltage curves of a carbon nanotube device in $ABTS^{2-}$ alone and as a function of time as the $ABTS^{2-}$ is oxidized by the laccase in solution.

The Isd vs. Vg curve of a semiconducting single-walled carbon nanotube device in the presence of 5 mM $ABTS^{-2}$ in 50 mM Glycine pH=3 was measured as a baseline and is shown in FIG. 9. An adjacent electrode served as a liquid gate. Then two solutions, one containing 10 mM $ABTS^{-2}$ in 50 mM Glycine, pH 3 and the other containing 10 µg/mL laccase in 50 mM Glycine, pH 3 were mixed just external to and pumped into the liquid chamber of the flow cell in contact with the device. The flow was stopped and the evolution of the Isd vs. Vg curve followed as a function of time. As time elapsed, a shift of the turn-on of the current toward positive gate voltages was observed. This shift is analogous to that observed in FIG. 7 where the biotinylated laccase was attached to the $SiO_2$ surface of the chip via the biotin-streptavidin link. The results of this experiment show that the presence of laccase molecules on the surface of the carbon nanotube is not required for laccase-mediated redox sensing. Instead, the enzyme molecules can be placed in any convenient location in the device, provided it is within 100 µm of the nanotubes to allow for diffusion of the redox mediator to the nanotubes on the seconds time scale (distance calculated from the expected diffusion coefficients of $ABTS^{-1}$ and $ABTS^{-2}$).

Example 7

Comparison of the Changes in Electronic and Optical Properties of Single-Walled Carbon Nanotubes during Oxidation A test was developed to show that the modulation of the electronic properties of the nanotubes comes from the oxidation and reduction of the nanotubes themselves. This was done by comparing the change in conductance as a function of time for carbon nanotubes in contact with redox mediators in solution to optical changes occurring in suspended nanotubes under the same conditions. We have previously shown that the oxidation and reduction of single-walled carbon nanotubes can be followed by their Vis/NIR absorbance spectra, where the E11 transitions disappear as the nanotubes are oxidized (M. Zheng and B. A. Diner, 2004, JACS 126, 15490-15494). HiPco single-walled nanotubes (Carbon Nanotechnologies Incorporated CNI, Houston Tex.) were surfactant-dispersed and suspended in 50 mM Glycine pH 9.0. The nanotubes under these conditions are partially oxidized, due to the $O_2/2H_2O$ redox couple, which interacts very slowly with the nanotubes. The suspension was then exposed to 1 mM $K_3Fe(CN)_6$ which resulted in a bleaching of the E11 absorbance band (FIG. 10A). A time course for the bleaching was observed at 1138 nm for ten minutes following the addition of 1 mM $K_3Fe(CN)_6$. The addition of 1 mM $K_4Fe(CN)_6$ to a fresh sample produced an evolution in the opposite direction, consistent with a reduction of the partially oxidized nanotubes. The time course of the optical changes was also measured following the addition of a lower concentration of ferricyanide (0.1 mM) such that the time course could be followed more completely, consistent with addition of oxidant and mixing by hand (FIG. 10B). The half time of the bleaching was about 2 min. FIG. 11 shows that upon addition of 0.1 mM $K_3Fe(CN)_6$ to a single-walled carbon nanotube based device there was also a slow evolution of the conductance to higher values with a half time also of about 2 min. This comparison showed that the change in the conductance of the carbon nanotube device in the presence of ferricyanide is due to the oxidation of the nanotubes.

Example 8

Discovery of Organic Inhibitors of Laccase and Testing with Linker

High potential quinones/quinols were screened to identify those with characteristics that would be suitable for use as an inhibitor of laccase, to be used in an activity switch. Potential inhibitors were chosen from a set of molecules with reduction potentials high enough so as not to be oxidized by laccase in the presence of $O_2$; a reduction potential greater than that of the copper centers of *Trametes versicolor* laccase, (0.78-0.79 V vs. NHE). Potential inhibitors were tested for the following characteristics:
1) A dissociation constant <50 µM, well below the dissociation constant, $K_d$ of 120-240 µM of the laccase substrate $ABTS^{-2}$.
2) Retention of inhibitor activity when tethered to a linker that would be tethered to DNA.

Compounds were evaluated by varying the concentrations of inhibitor and substrate ($ABTS^{-2}$) and measuring under each condition the rate of $ABTS^{-2}$ oxidation. Plots of the reciprocal of the rate versus the inhibitor concentration at various substrate concentrations gave, at the intersection point, $-Ki$, the negative of the dissociation constant of the inhibitor. Tetrachloro-o-quinol and tetrafluoro-o-quinol, shown in Diagram I, had Kds, of 7-9 µM and 2.5 µM, respectively, as determined from the data in FIG. 12.

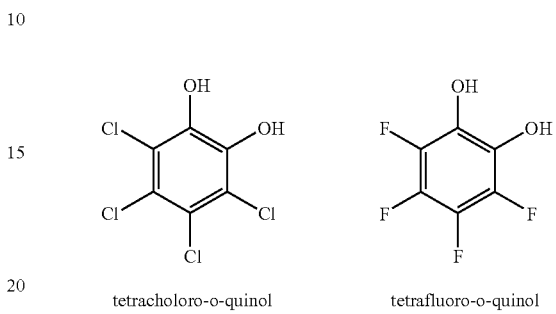

Diagram I

Since tetrachloro-o-quinol was an effective inhibitor, tetrachloro-p-quinol was also tested. The latter was inactive as an inhibitor, indicating the likely importance of having the hydroxyl groups ortho to each other. This arrangement strongly suggested a role for these groups in the coordination of the Type I copper center of the enzyme. This conclusion was strengthened by the observation that the binding of tetrachloro-o-quinol to laccase caused a decrease in the amplitude of the laccase 600 nm absorbance peak, dominated by a charge-transfer band involving the Type I copper center and its cysteinyl ligand.

Preparation of 3,4-dihydroxy-2,6-dichloro-benzaldehyde as starting point for construction of inhibitor for switch The compound 3,4-dihydroxy-2,6-dichloro-benzaldehyde (Diagram II) has a structure which we have determined to be effective in laccase inhibition (described above) as well as a functional group for preparation of the activity switch.

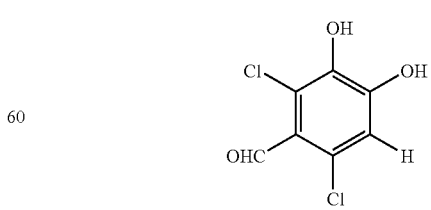

3,4-dihydroxy-2,6-dichloro-benzaldehyde

Diagram II

A test of the ability to attach a linker to the inhibitor and retain inhibitory activity involved synthesis of 3,4-di-OH-2, 6-di-Cl-benzaldehyde followed by coupling it to Biotin-dPEG₄-hydrazide (Diagram III), thereby adding a tail of ~2.5 nm to the inhibitor.

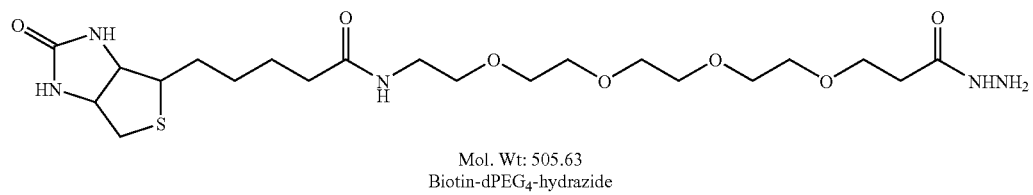

Mol. Wt: 505.63
Biotin-dPEG₄-hydrazide

Diagram III

Into an oven-dried, three-neck round bottom flask, fitted with a thermometer, 1.0 g (4.52 mmol; Aldrich, Milwaukee, Wis.) of 2,6-dichloro-3-hydroxy-4-methoxybenzaldehyde and 45 mL of dichloromethane were added under nitrogen atmosphere. The solution was cooled to −65° C. and 1.32 mL (14 mmol) of boron tribromide was added dropwise. The reaction mixture was left to warm up slowly to room temperature with stirring for 16 hours. The reaction mixture was carefully quenched with the addition of 5 mL of water, then transferred to a single-neck round bottom flask and volatiles were removed in vacuo. The residue was taken up with 50 mL of ethylacetate and washed three times with water and two times with brine. The organic layer was dried over MgSO₄, then concentrated to yield 0.9 g (96%) of crude 2,6-dichloro-3,4-dihydroxybenzaldehyde, as an off-white solid, which was used without further purification. $^1$H-NMR δ (d₆-acetone): 6.85 (1H, s), 9.1 (2H, br s), 10.2 (1H,s). Melting point=213-215° C.

Attachment of 2,6-dichloro-3,4-dihydroxybenzaldehyde to Biotin-dPEG₄™-hydrazide Biotin-dPEG₄™-hydrazide (15 mg, 30 nmol, Quanta BioDesign, Ltd.; Powell, Ohio) and 2,6-dichloro-3,4-dihydroxybenzaldehyde (6.2 mg, 30 nmol) were dissolved in CH₂Cl₂ (1.5 mL) and stirred at ambient temperature for 18 hours. After the addition of sodium cyanoborohydride (6 mg, 100 nmol), the reaction mixture was stirred for an additional 2 hours, washed with water (2×0.5 mL) and dried on a rotavap. The 3,4-di-OH-2,6-di-Cl-benzaldehyde coupled Biotin-dPEG₄-hydrazide was evaluated by varying the concentrations of inhibitor and substrate (ABTS$^{-2}$) and measuring under each condition the rate of ABTS$^{-2}$ oxidation. Kinetic plots of 1/V versus inhibitor concentration, [I], showed a Kd of 4.5 to 7.5 µM. Thus the addition of a ~2.5 nm tail to the inhibitor did not impair the ability of the molecule to inhibit laccase activity.

Example 9

Preparation of Activity Switch

Attachment of DNA to Laccase

A single-stranded oligonucleotide probe was attached to laccase using aldehyde-hydrazide attachment chemistry. Laccase from *Trametes versicolor* (6.2 µM; Wacker Chemie GmbH, Munich, Germany) was treated with NaIO₄ (120 mM) in 100 mM Na Acetate pH 5 for 1 h at room temperature. Ethylene glycol (120 mM) was then added to quench the unreacted periodate. The oxidized laccase washed twice by diluting in 100 mM Na Acetate pH 5.0 and concentrating in an Amicon Ultra-4 (30,000 MWCO) (Millipore; Billerica, Mass.). A third wash was carried out in 0.5 M NaPO₄, pH 7.4. Overall wash was 1600-fold.

Periodate-treated laccase (32.5 µM) was treated separately with 325 µM of oligonucleotides 27(SEQ ID NO:1 with 3'-Cy3), 28 (SEQ ID NO:1), 32 (SEQ ID NO:6), 50 (SEQ ID NO:5 with 3'-Cy3), and 61 (SEQ ID NO:7), each containing a hydrazide group at the 5' end (C6 I-link, Integrated DNA Technologies, Inc.) in 200 µL for 1 h at room temperature. Two µL of 5 M NaBH₃CN in 1 M NaOH was added (final concentration 50 mM) and incubated at room temperature for 30 min. Unreacted aldehyde sites were then removed by the addition of 1 µL of 3 M ethanolamine, pH 7 (final concentration 15 mM) followed by 30 min incubation at room temperature. The laccase was then washed 3-times in an Amicon Ultra-4 (30,000 MWCO) (Millipore) with 100 mM Na Acetate pH 5.0. Total wash 8000-fold.

The resulting preparation was analyzed by SDS-polyacrylamide gel electrophoresis. Staining the protein bands with Coomassie Blue showed that the molecular mass of the laccase was increased by this treatment. Staining of parallel lanes on the same gel with ethydium bromide revealed that the same protein bands also contained oligonucleotides. Both indicated that the oligonucleotides were indeed attached to laccase. The enzymatic activity of the laccase/oligo adduct was assayed using the ABTS$^{-2}$ substrate and was shown in all cases to be ≧50% of the starting activity.

Inhibitor Linking to DNA

The 3,4-di-OH-2,6-di-Cl-benzaldehyde prepared above is coupled to Maleimide-dPEG₄-NHS ester (as shown in Diagram IV), followed by coupling to an oligonucleotide. Maleimide-dPEG₄-NHS-ester (Quanta Biodesign Inc.; Powell, Ohio) is derivatized with hydrazine to give the hydrazide. The product is reacted with 3,4-di-OH-2,6-diCl-benzaldehyde to give the hydrazone. This product is either used directly, or is reduced to the substituted hydrazide.

Strategy for inhibitor coupling to 5'-hydrazide linked
DNA thiolated at 3' end

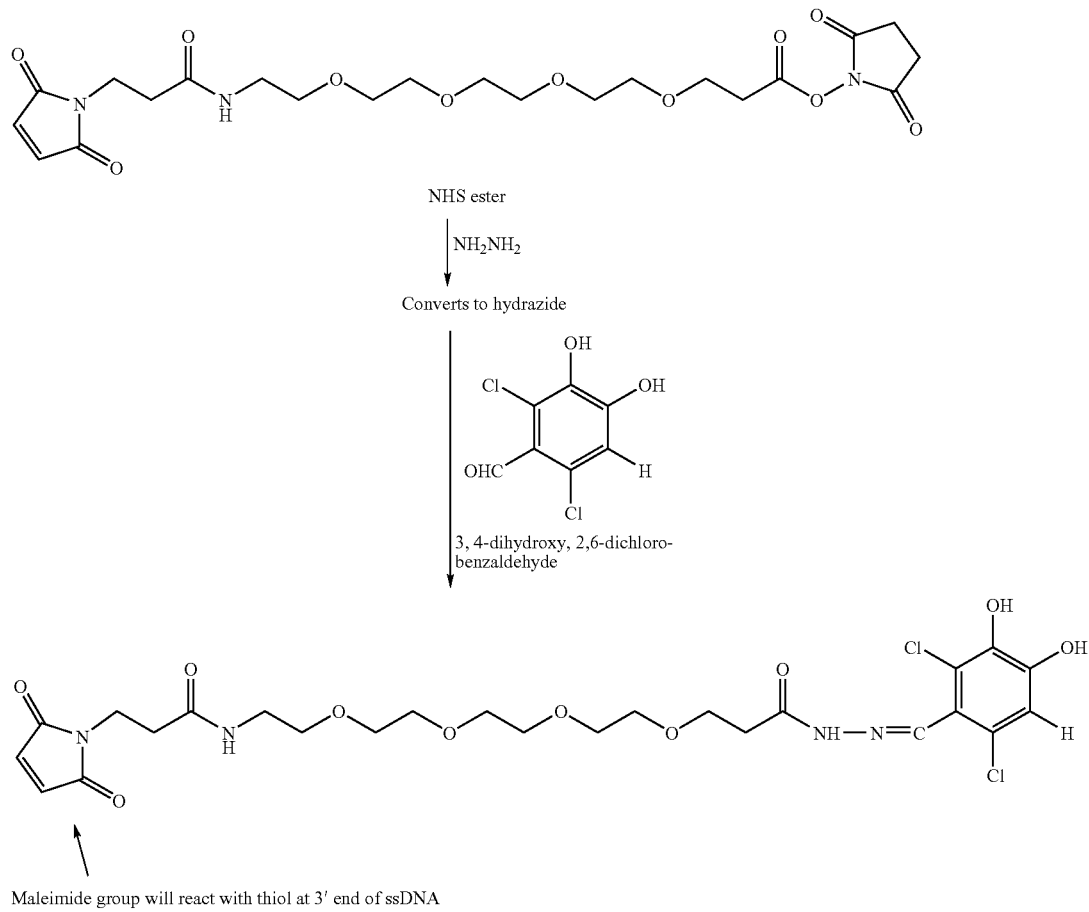

Maleimide group will react with thiol at 3' end of ssDNA

Diagram IV

The maleimide group of the product is then coupled to the thiol group of a 5'-hydrazide, 3'-thiol coupled oligonucleotide. This product is then coupled through the hydrazide group to aldehydes of periodate-oxidized laccase, as described above.

What is claimed is:

1. A nanosensor for detecting the presence of an analyte said nanosensor comprising at least two electrodes connected by an electrically conducting path comprised of one or more carbon nanotubes wherein at least one of said carbon nanotubes is semiconducting, and wherein the carbon nanotube is in contact with an effector solution having a redox potential; and wherein said nanosensor is capable of detecting the presence of said analyte with said analyte neither directly bound on said carbon nanotube nor in close proximity to said carbon nanotube.

2. The nanosensor of claim 1 wherein said analyte is a redox-active analyte.

3. The nanosensor of claim 2 wherein said nanosensor further comprises at least one redox reporter having a redox-active analyte as a substrate.

4. A nanosensor according to claim 2 wherein the nanosensor optionally comprises a redox mediator.

5. The nanosensor of claim 1 wherein said nanosensor further comprises:
   i) a redox reporter having an activity switch comprising an analyte receptor and a reporter inhibitor; and
   ii) a redox-active substrate that is a substrate of said redox reporter.

6. A nanosensor according to claim 3 or 5 wherein the redox reporter is an enzyme.

7. A nanosensor according to claim 6 wherein the enzyme is selected from the group consisting of laccase, glucose oxidase, cholesterol oxidase, alcohol dehydrogenase, lactate dehydrogenase, bilirubin oxidase, and D-amino acid oxidase.

8. A nanosensor according to claim 3 or 5 wherein the redox-active substrate and co-substrate are selected from the group consisting of ABTS, $O_2$, DOPIP, $NAD^+$ (NADH), $NADP^+$ (NADPH), flavin, o-, m- and p-quinones, glucose, cholesterol, bilirubin, alcohols, and D-amino acids.

9. The nanosensor of claim 1 wherein said analyte is a redox catalytic analyte and wherein said nanosensor further comprises a redox-active substrate that is a substrate of said redox catalytic analyte.

10. A nanosensor according to any of claims 2, 3, 5, or 9 optionally comprising a gate electrode.

11. A nanosensor according to any of claims 2, 3, 5, or 9 wherein the carbon nanotube is suspended between at least two electrodes.

12. A nanosensor according to any of claims 2, 3, 5, or 9 wherein the carbon nanotube is supported on a support.

13. A nanosensor according to claim 12 wherein the support is comprised of materials selected from the group consisting of silicon, polysilicon, silicon dioxide, silicon nitride, polymeric materials, glass, agarose, nitrocellulose, nylon, and insulating materials.

14. A nanosensor according to any of claims 2, 3, 5, or 9 wherein the redox potential of the effector solution affects the density of charge carriers on the carbon nanotube.

15. A nanosensor according to any of claims 2, 3, 5, or 9 wherein the carbon nanotube is substantially free of metal.

16. A method for detecting an analyte comprising:
   a) providing a nanosensor comprising at least two electrodes connected by an electrically conducting path comprised of one or more carbon nanotubes wherein at least one of said carbon nanotubes is semiconducting, and wherein the carbon nanotube is in contact with an effector solution having a redox potential and wherein the carbon nanotube has a baseline conductance;
   b) providing a sample suspected of containing an analyte;
   c) contacting the sample of (b) with the nanosensor of (a) wherein the redox potential of the carbon nanotube or effector solution is altered resulting in a change in the conductance of the carbon nanotube with respect to the baseline conductance, wherein said change in conductance occurs with said analyte neither directly bound on said carbon nanotube nor in close proximity to said carbon nanotube; and d) measuring the change in conductance of the carbon nanotube with respect to the baseline conductance whereby the presence of the analyte is detected.

17. The method of claim 16 wherein said analyte is a redox-active analyte.

18. The method of claim 17 wherein said nanosensor of step a) further comprises a redox reporter having a redox-active analyte as a substrate; and wherein said contacting of step c) comprises contacting the sample of b) with the redox reporter of a) wherein the redox potential of the effector solution is altered resulting in a change in the conductance of the carbon nanotube with respect to the baseline conductance.

19. A method according to claim 17 wherein the nanosensor optionally comprises a redox mediator.

20. The method of claim 16 wherein said nanosensor of step a) further comprises
   i) a redox reporter having an activity switch comprising an analyte receptor and a reporter inhibitor;
   ii) a redox-active substrate that is a substrate of the redox reporter;
and wherein the analyte of the sample of step b) binds to the analyte receptor of the activity switch wherein the redox reporter becomes active; and wherein said contacting of step c) comprises contacting the sample of b) with the redox reporter of a) wherein the redox potential of the effector is altered resulting in a change in the conductance of the carbon nanotube with respect to the baseline conductance.

21. A method according to claim 18 or 20 wherein the redox reporter is an enzyme.

22. A method according to claim 21 wherein the enzyme is selected from the group consisting of laccase, glucose oxidase, bilirubin oxidase, cholesterol oxidase, alcohol dehydrogenase, lactate dehydrogenase, and D-amino acid oxidase.

23. The method of claim 16 wherein said analyte is a redox catalytic analyte; wherein said nanosensor of step a) further comprises a redox-active substrate that is a substrate of a redox catalytic analyte; and wherein said contacting of step c) comprises contacting the sample of b) with the redox-active substrate of a) and a co-substrate wherein the redox potential of the effector solution is altered resulting in a change in the conductance of the carbon nanotube with respect to the baseline conductance.

24. A method according to claim 20 or 23 or wherein the redox-active substrate is selected from the group consisting of ABTS, $O_2$, DOPIP, $NAD^+$ (NADH), $NADP^+$ (NADPH), flavin, o-, m- and p-quinones, glucose, bilirubin, cholesterol, alcohols, and D-amino acids.

25. A method according to any of claims 17, 18, 20, or 23 wherein the carbon nanotube is substantially free of metal.

26. A method according to any of claims 17, 18, 20, or 23 wherein the carbon nanotube is optionally supported on a support.

27. A method according to claim 26 wherein the support is comprised of materials selected from the group consisting of silicon, polysilicon, silicon dioxide, silicon nitride, polymeric materials, glass, agarose, nitrocellulose, nylon, and insulating materials.

* * * * *

UNITED STATES PATENT AND TRADEMARK OFFICE
CERTIFICATE OF CORRECTION

PATENT NO. : 7,638,036 B2
APPLICATION NO. : 11/240287
DATED : December 29, 2009
INVENTOR(S) : Boussaad et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 920 days.

Signed and Sealed this

Ninth Day of November, 2010

David J. Kappos
*Director of the United States Patent and Trademark Office*

```
                            SEQUENCE LISTING

<160> NUMBER OF SEQ ID NOS: 4

<210> SEQ ID NO 1
<211> LENGTH: 18
<212> TYPE: DNA
<213> ORGANISM: artificial sequence
<220> FEATURE:
<223> OTHER INFORMATION: synthetic oligo

<400> SEQUENCE: 1
cgctgtgatg gtggcccc                                                  18

<210> SEQ ID NO 2
<211> LENGTH: 28
<212> TYPE: DNA
```

```
<213> ORGANISM: artificial sequence
<220> FEATURE:
<223> OTHER INFORMATION: synthetic oligo

<400> SEQUENCE: 2
tttttttttt cgctgtgatg gtggcccc                                      28

<210> SEQ ID NO 3
<211> LENGTH: 28
<212> TYPE: DNA
<213> ORGANISM: artificial sequence
<220> FEATURE:
<223> OTHER INFORMATION: synthetic oligo

<400> SEQUENCE: 3
tttttttttt cgctgtgatg gtggcccc                                      28

<210> SEQ ID NO 4
<211> LENGTH: 36
<212> TYPE: DNA
<213> ORGANISM: artificial sequence
<220> FEATURE:
<223> OTHER INFORMATION: synthetic oligo

<400> SEQUENCE: 4
tttttttttt ttttcctcgt cagatttgtc cttgca                             36
```